(12) United States Patent
Vestgaarden

(10) Patent No.: US 8,623,053 B2
(45) Date of Patent: *Jan. 7, 2014

(54) METHOD AND APPARATUS FOR SPINAL FACET FUSION

(75) Inventor: Tov Inge Vestgaarden, Madeira Beach, FL (US)

(73) Assignee: VG Innovations, LLC, St. Petersburg, FL (US)

( * ) Notice: Subject to any disclaimer, the term of this patent is extended or adjusted under 35 U.S.C. 154(b) by 97 days.

This patent is subject to a terminal disclaimer.

(21) Appl. No.: 13/276,610

(22) Filed: Oct. 19, 2011

(65) Prior Publication Data

US 2012/0271351 A1    Oct. 25, 2012

Related U.S. Application Data

(63) Continuation-in-part of application No. 12/154,372, filed on May 22, 2008, now Pat. No. 8,162,981.

(60) Provisional application No. 60/939,615, filed on May 22, 2007, provisional application No. 61/394,419, filed on Oct. 19, 2010.

(51) Int. Cl.
*A61B 17/70* (2006.01)
*A61B 17/88* (2006.01)

(52) U.S. Cl.
USPC ............................ 606/247; 606/279

(58) Field of Classification Search
USPC ............ 606/246–249, 95–99, 84, 86 A, 279; 623/17.11, 17.16; 128/898
See application file for complete search history.

(56) References Cited

U.S. PATENT DOCUMENTS

| | | | |
|---|---|---|---|
| 7,674,296 B2* | 3/2010 | Rhoda et al. | 623/17.15 |
| 7,691,148 B2* | 4/2010 | Michelson | 623/17.16 |
| 7,708,761 B2* | 5/2010 | Petersen | 606/247 |
| 7,758,648 B2* | 7/2010 | Castleman et al. | 623/17.16 |
| 7,850,736 B2* | 12/2010 | Heinz | 623/17.36 |
| 8,162,981 B2* | 4/2012 | Vestgaarden | 606/247 |
| 2005/0149192 A1* | 7/2005 | Zucherman et al. | 623/17.11 |
| 2006/0085068 A1 | 4/2006 | Barry | |
| 2006/0111782 A1 | 5/2006 | Petersen | |
| 2007/0083265 A1 | 4/2007 | Malone | |
| 2008/0154374 A1 | 6/2008 | Labrom | |
| 2008/0255666 A1* | 10/2008 | Fisher et al. | 623/17.16 |
| 2009/0036927 A1 | 2/2009 | Vestgaarden | |

OTHER PUBLICATIONS

International Search Report with date of mailing May 24, 2012 pertaining to international application No. PCT/US2011/056878 with international filed of Oct. 19, 2011.

(Continued)

*Primary Examiner* — Pedro Philogene
(74) *Attorney, Agent, or Firm* — Ronald E. Smith; Smith & Hopen, P.A.

(57) ABSTRACT

A spinal facet fusion implant includes an elongated main body having a distal end, a proximal end and a longitudinal axis extending between the distal end and the proximal end. The main body has a cross-sectional profile characterized by a primary axis and a secondary axis. At least one stabilizer extends radially outwardly from the main body in the secondary axis. The main body has a length along the primary axis that is less than the combined width of the spinal facets making up a facet joint. The stabilizer has a width that is sized to make a press fit into the gap between the spinal facets making up a facet joint.

38 Claims, 58 Drawing Sheets

(56) References Cited

OTHER PUBLICATIONS

Stein, M.; Elliott, D.; Glen, J.; Morava-Protzner, I. Young Investigator Award: Percutaneous Facet Joint Fusion: Preliminary Experience, Journal of Vascular and Interventional Radiology, vol. 4, Issue 1, Jan. 1993, pp. 69-74.

* cited by examiner

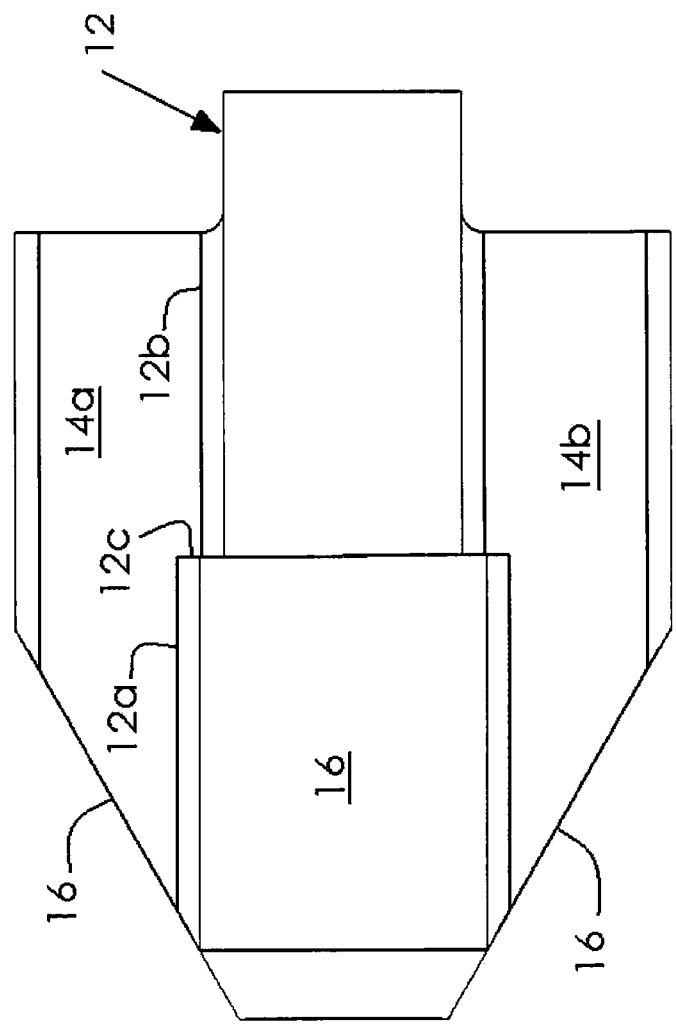

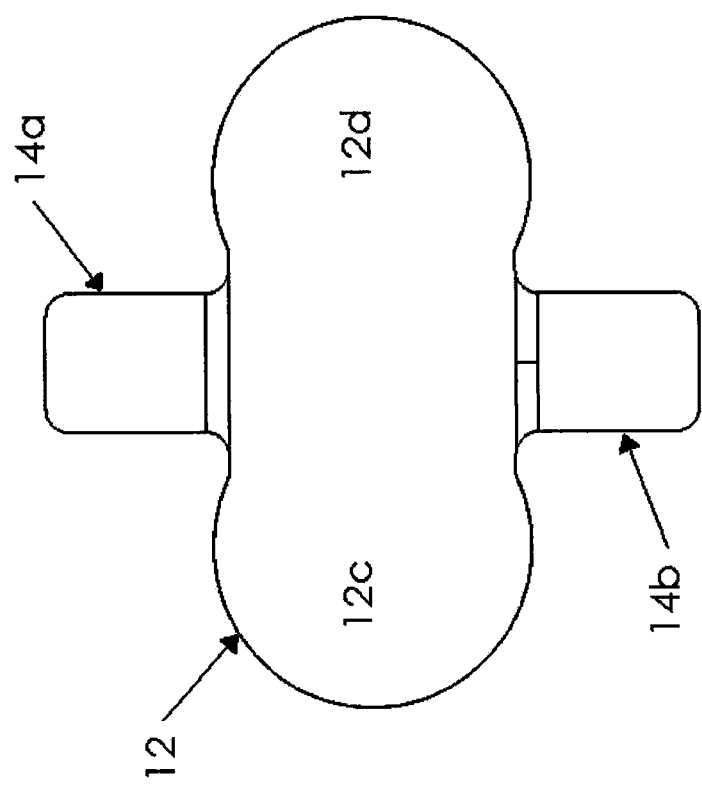

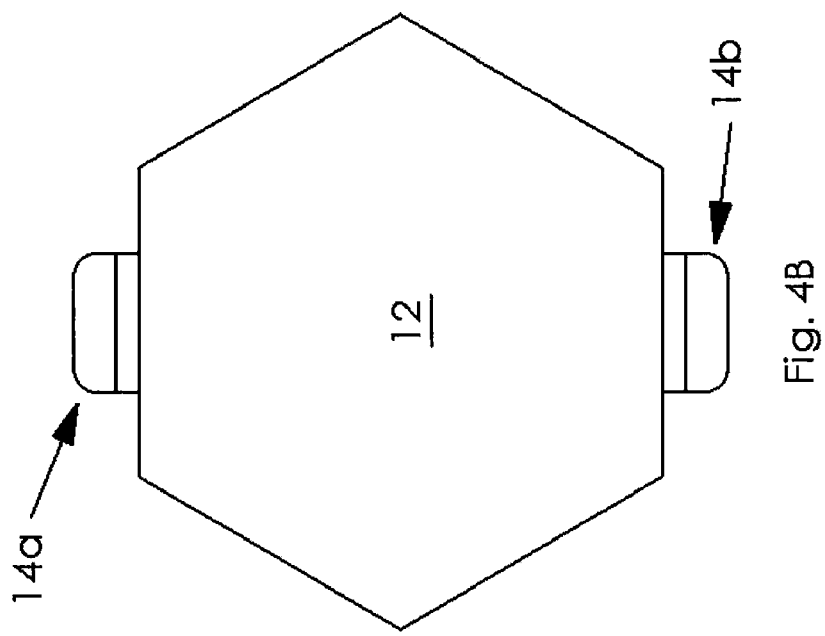

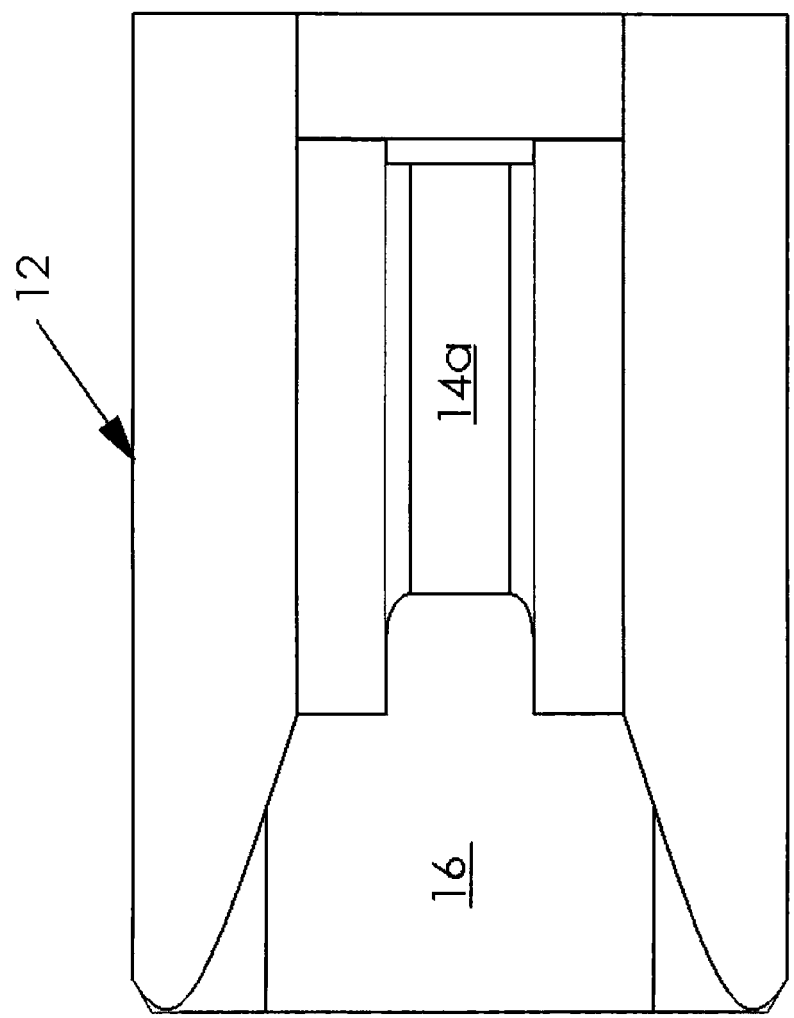

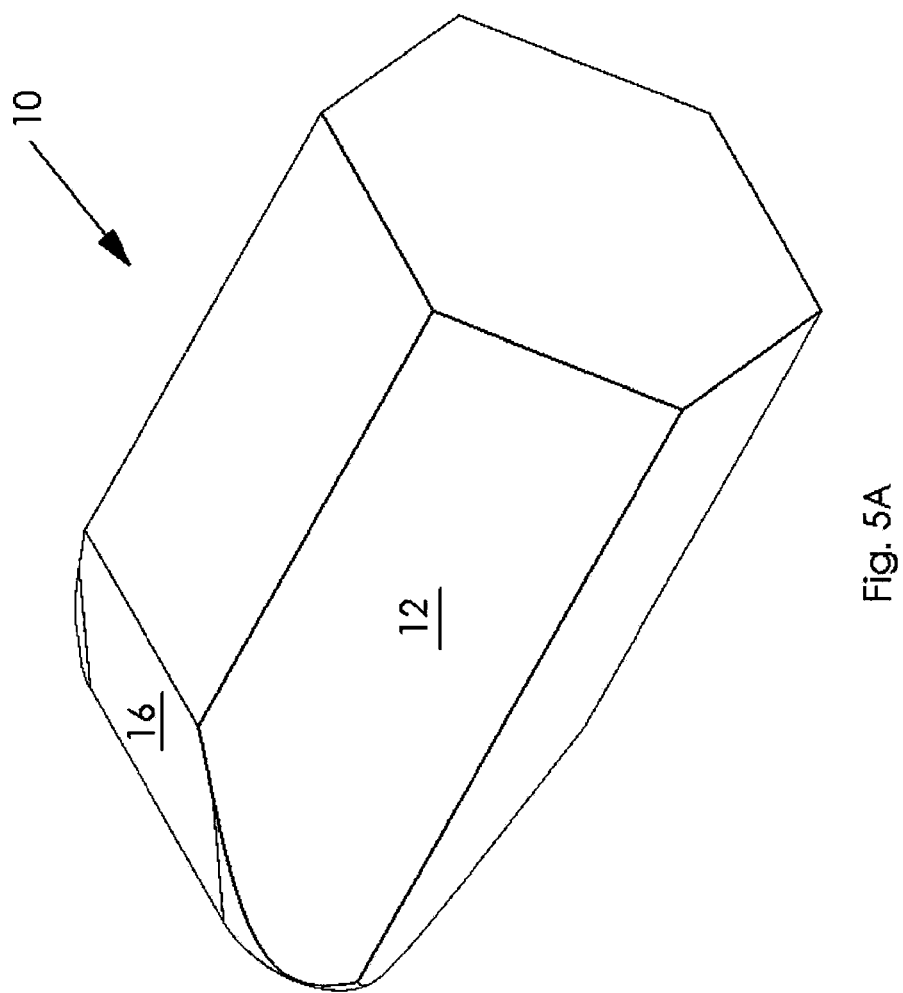

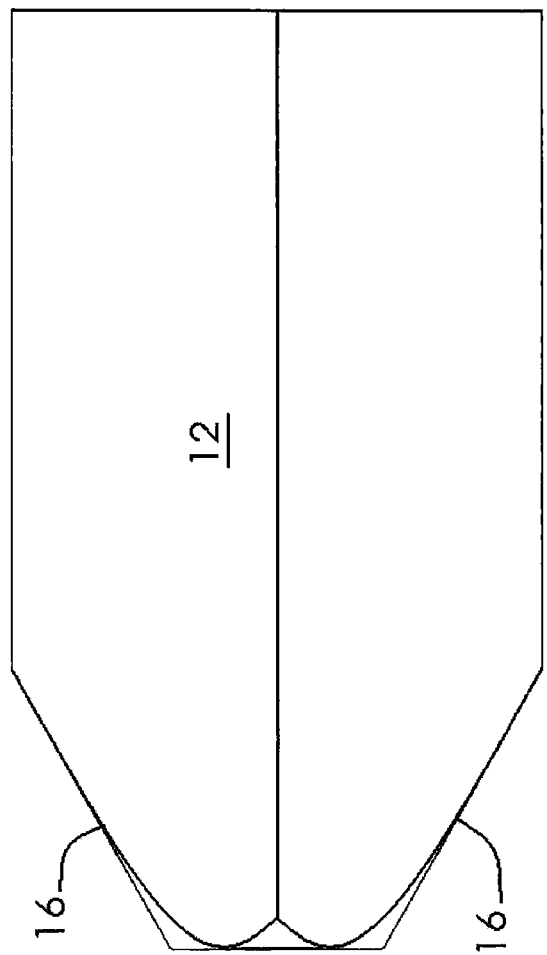

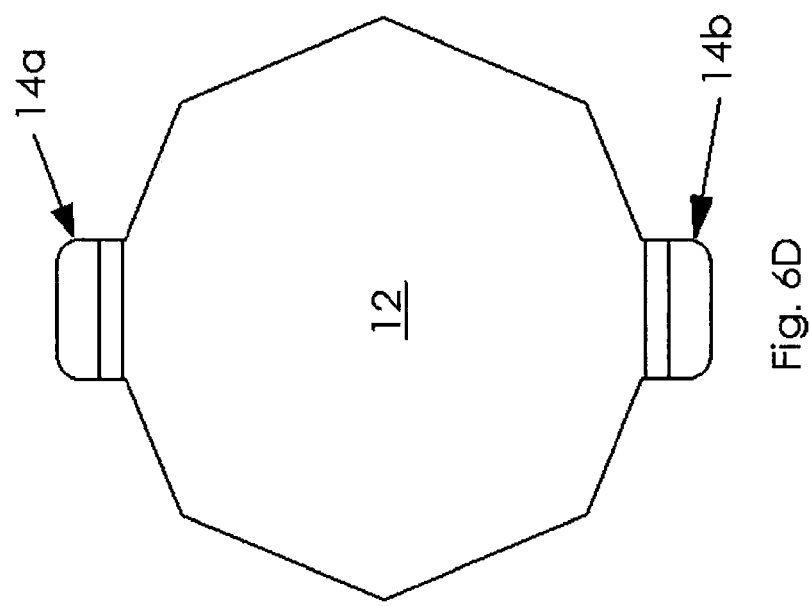

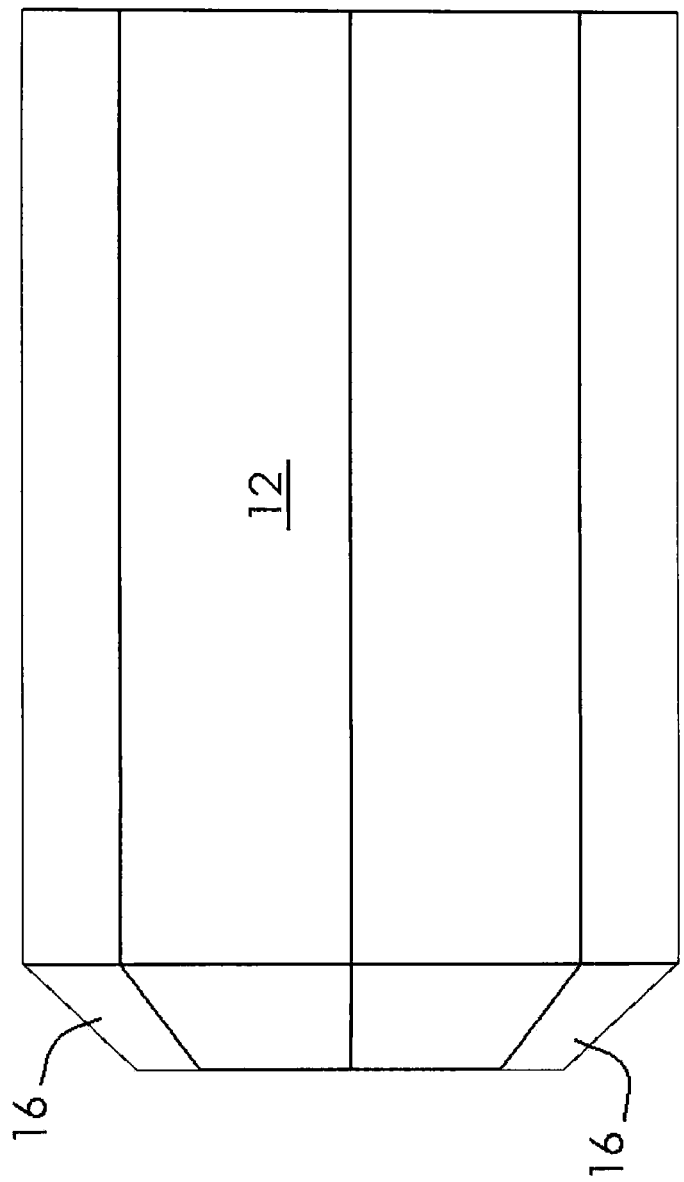

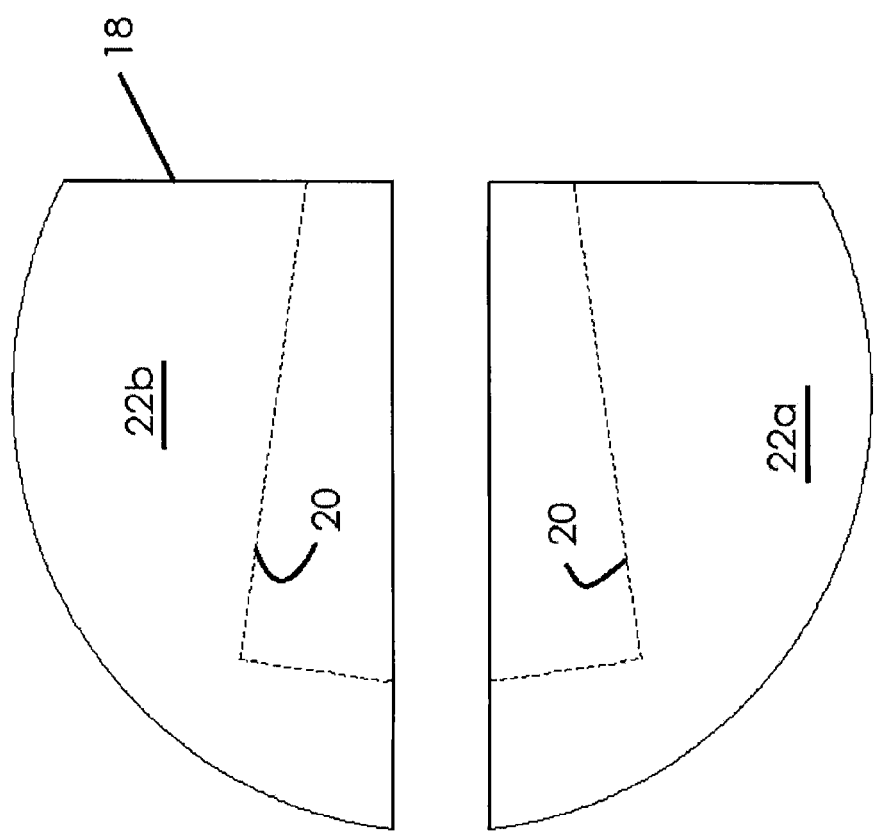

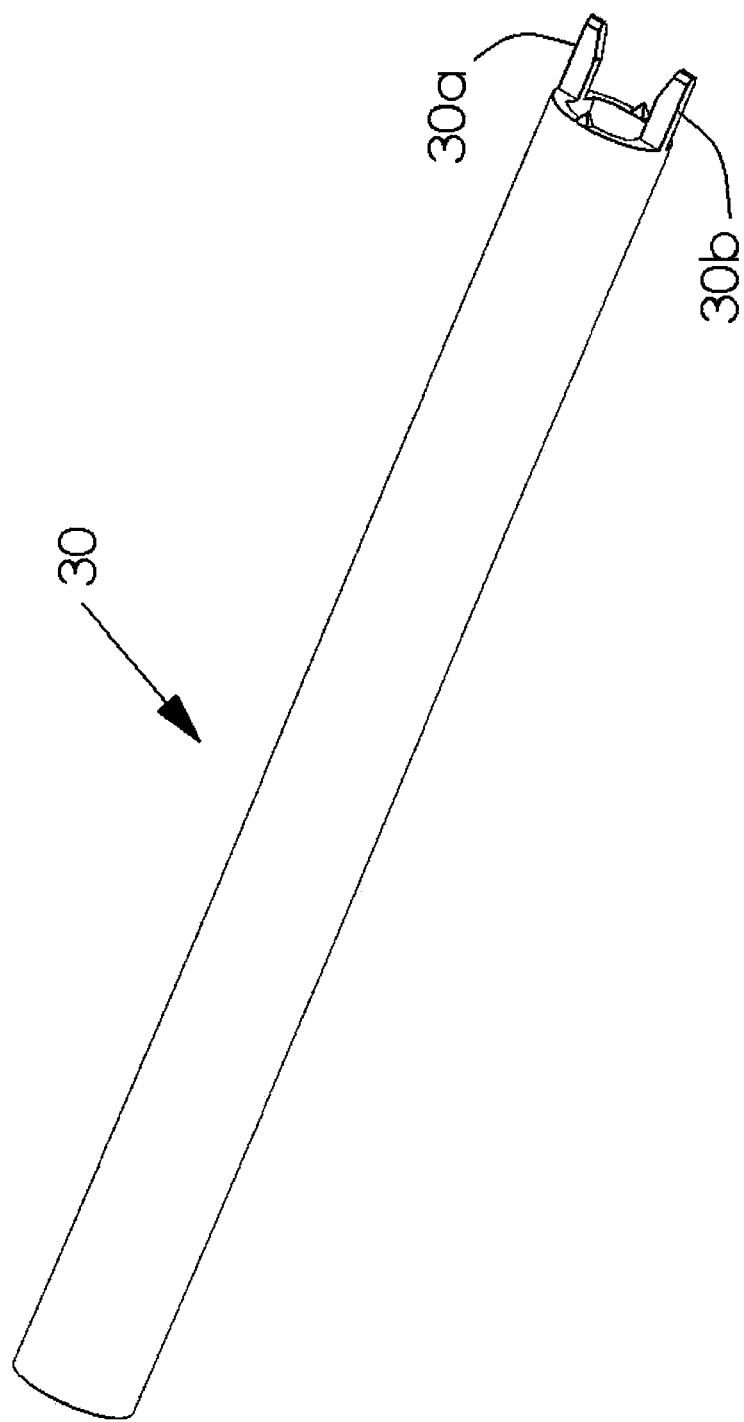

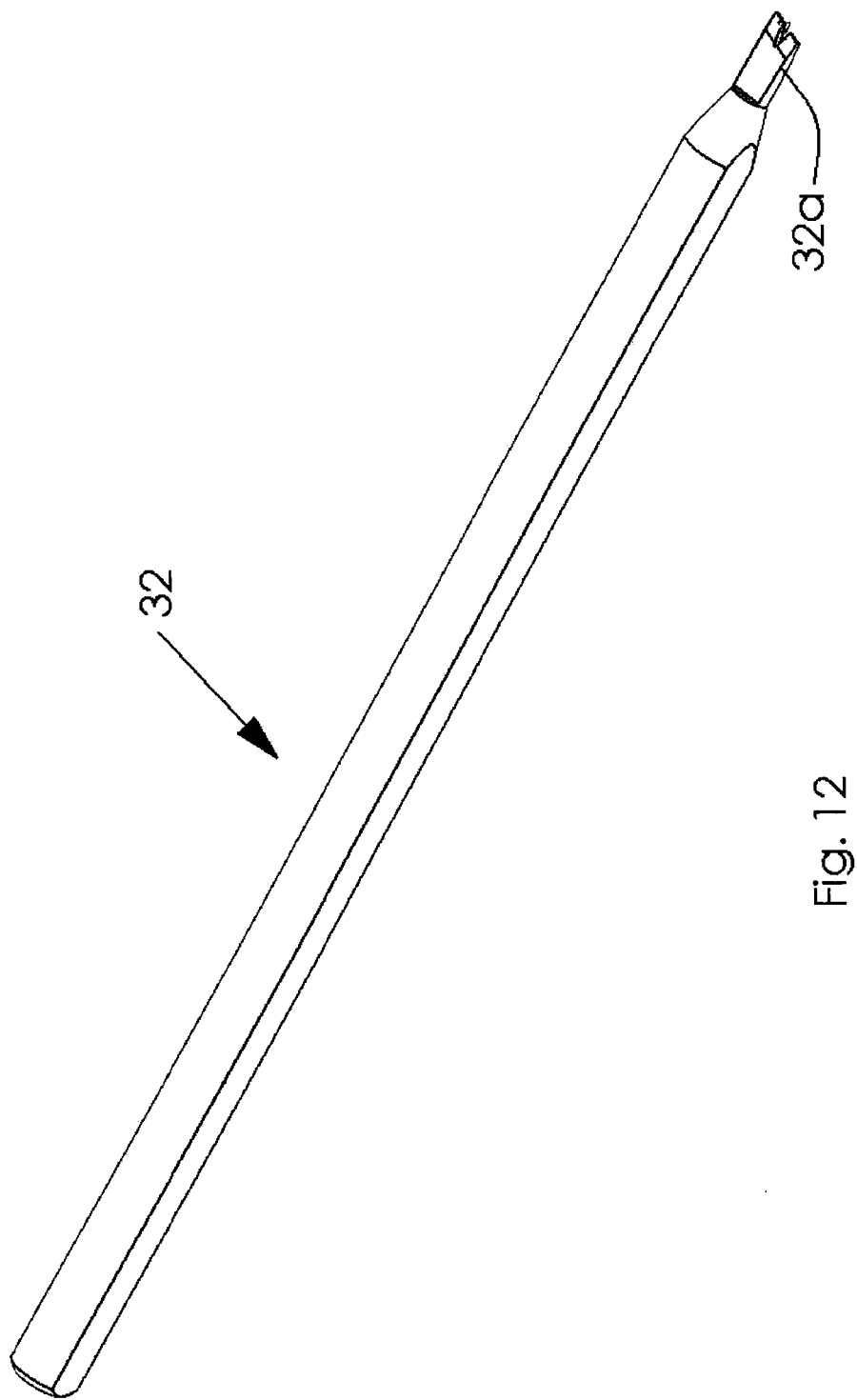

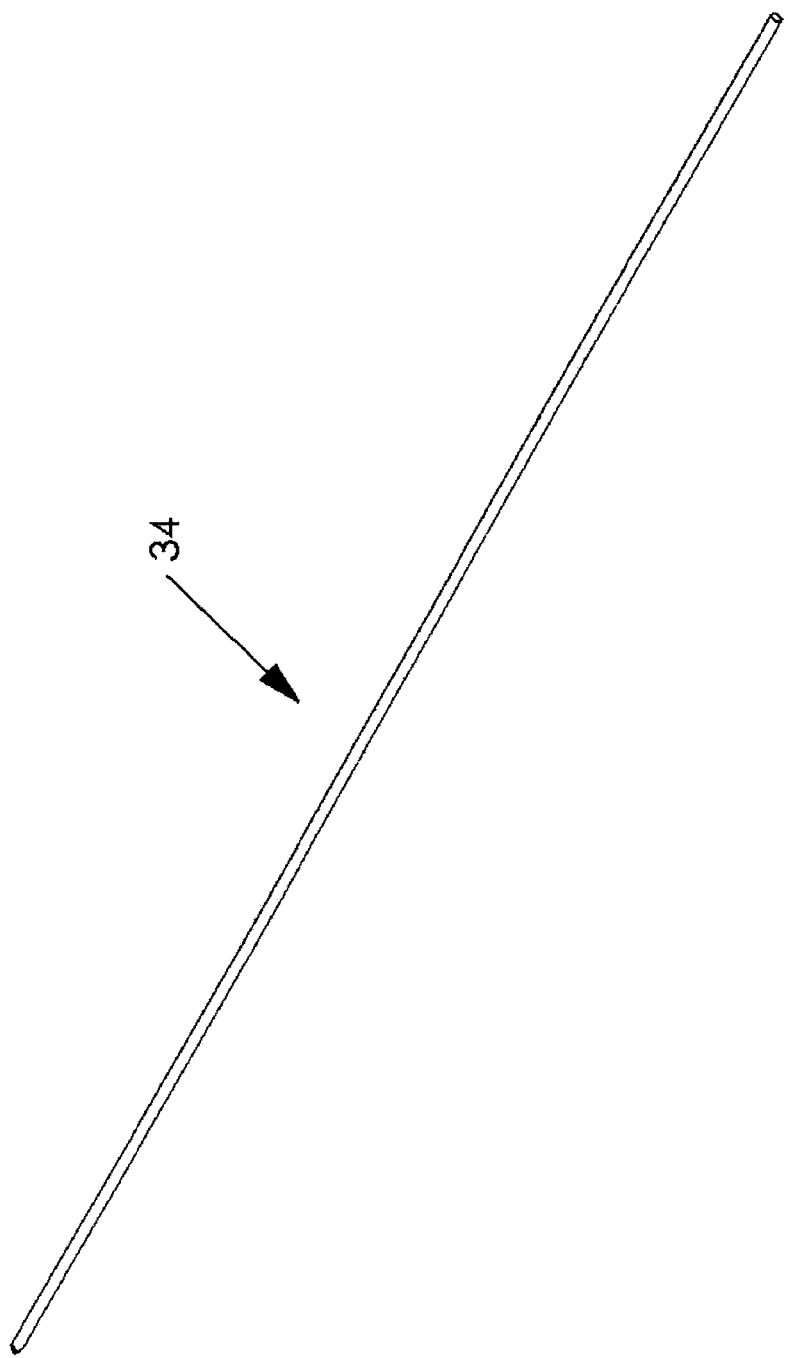

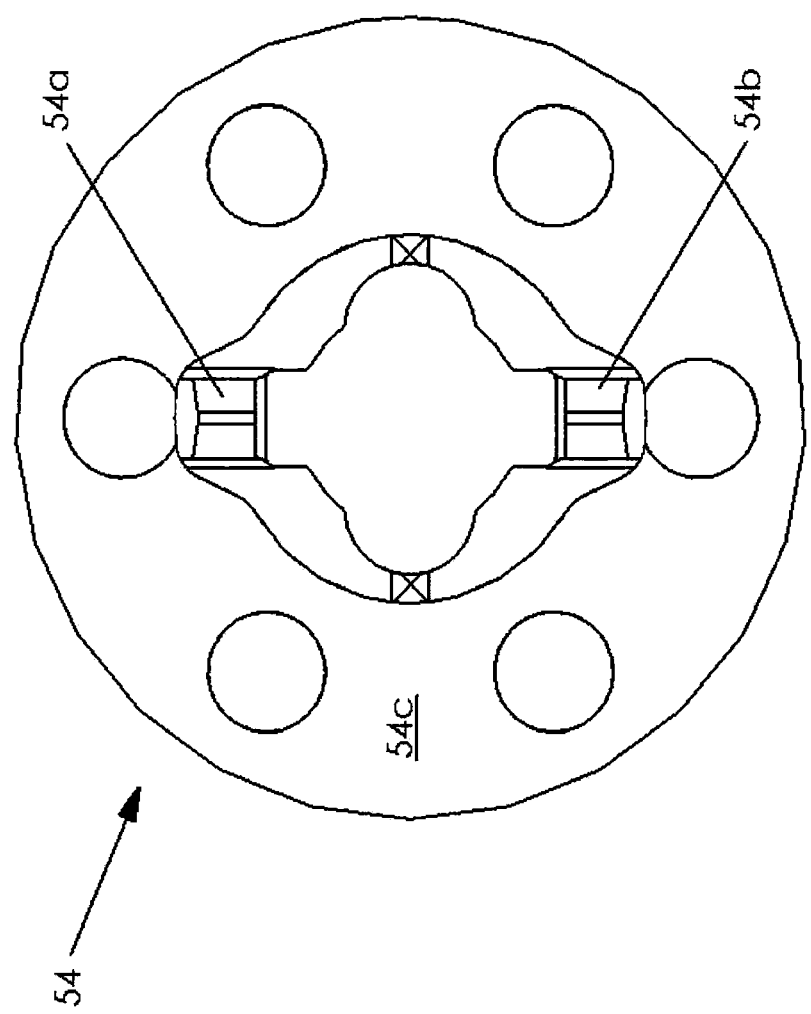

METHOD AND APPARATUS FOR SPINAL FACET FUSION

CROSS-REFERENCE TO RELATED APPLICATIONS

This patent application is a continuation-in-part of and claims benefit of pending prior U.S. non-provisional patent application Ser. No. 12/154,372, filed May 22, 2008 by Tov Vestgaarden for Method and Apparatus for Spinal Facet Fusion, which claims priority to U.S. provisional patent application No. 60/939,615, filed May 22, 2007 by the same inventor for Percutaneous Spinal Facet Fixation Device for Facet Fusion. This application also claims priority to, and is a non-provisional of pending U.S. provisional patent application No. 61/394,419, filed Oct. 19, 2010 by the same inventor for Open, Minimally Invasive, Percutaneous, Arthroscopic Spinal Facet Fusion Device and Delivery Method, all of which applications are hereby incorporated herein by reference.

BACKGROUND OF THE INVENTION

1. Field of the Invention

This invention relates to surgical methods and apparatus in general, and more particularly to surgical methods and apparatus for fusing spinal facets.

2. Description of the Related Art

Disc herniation is a condition where a spinal disc bulges from between two vertebral bodies and impinges on adjacent nerves, thereby causing pain. The current standard of care for surgically treating disc herniation in patients who have chronic pain and who have (or are likely to develop) associated spinal instability is spinal fixation. Spinal fixation procedures are intended to relieve the impingement on the nerves by removing the portion of the disc and/or bone responsible for compressing the neural structures and destabilizing the spine. The excised disc or bone is replaced with one or more intervertebral implants, or spacers, placed between the adjacent vertebral bodies.

In some cases, the spinal fixation leaves the affected spinal segment unstable. In this case, the spinal facets (i.e., the bony fins extending upwardly and downwardly from the rear of each vertebral body) can disengage with one another. The disengagement of the spinal facets can cause substantial pain to the patient. Furthermore, when left untreated, such disengagement of the spinal facets can result in the degeneration of the cartilage located between opposing facet surfaces, ultimately resulting in osteoarthritis, which can in turn lead to worsening pain for the patient.

Thus, where the patient suffers from spinal instability, it can be helpful to stabilize the facet joints as well as the vertebral bodies. The facet joints are frequently stabilized by fusing the spinal facets in position relative to one another.

In addition to providing stability, fusing the spinal facets can also be beneficial in other situations as well. By way of example but not limitation, osteoarthritis (a condition involving the degeneration, or wearing away, of the cartilage at the end of bones) frequently occurs in the facet joints. The prescribed treatment for osteoarthritis disorders depends on the location, severity and duration of the disorder. In some cases, non-operative procedures (including bed rest, medication, lifestyle modifications, exercise, physical therapy, chiropractic care and steroid injections) may be satisfactory treatment. However, in other cases, surgical intervention may be necessary. In cases where surgical intervention is prescribed, spinal facet fusion may be desirable.

A minimally-invasive, percutaneous approach for fusing spinal facets was proposed by Stein et al. ("Stein") in 1993. The Stein approach involved using a conical plug, made from cortical bone and disposed in a hole formed intermediate the spinal facet joint, to facilitate the fusing of opposing facet surfaces. However, the clinical success of this approach was limited. This is believed to be because the Stein approach did not adequately restrict facet motion. In particular, it is believed that movement of Stein's conical plug within its hole permitted unwanted facet movement to occur, thereby undermining facet fusion. Furthermore, the Stein approach also suffered from plug failure and plug migration.

Thus there is a need for a new and improved approach for effecting spinal facet fusion.

However, in view of the art considered as a whole at the time the present invention was made, it was not obvious to those of ordinary skill in the field of this invention how the shortcomings of the prior art could be overcome.

SUMMARY OF THE INVENTION

The long-standing but heretofore unfulfilled need for improved devices and methods for effecting spinal facet fusion is now met by a new, useful, and nonobvious invention.

The novel method and apparatus for effecting spinal facet fusion includes a novel spinal facet fusion implant for disposition between opposing articular surfaces of a facet joint to immobilize the facet joint and facilitate fusion between the opposing facets.

More particularly, in one form of the present invention, there is provided a spinal facet fusion implant that includes an elongated body having a distal end, a proximal end and a longitudinal axis extending between the distal end and the proximal end. The elongated body has a cross-sectional profile characterized by a primary axis and a secondary axis; and at least one stabilizer extends radially outwardly from the elongated body in the secondary axis.

The elongated body has a length along the primary axis that is less than the combined width of the spinal facets making up a facet joint.

The at least one stabilizer has a width which is sized to make a press fit into the gap between the spinal facets making up a facet joint.

A method for fusing a spinal facet joint includes the steps of providing a spinal facet fusion implant having an elongated body having a distal end, a proximal end and a longitudinal axis extending between the distal end and the proximal end. The method further includes the steps of providing the elongated body with a cross-sectional profile characterized by a primary axis and a secondary axis and providing at least one stabilizer that extends radially outwardly from the elongated body in the secondary axis.

The method steps further include the steps of forming the elongated body so that it has a length along the primary axis which is less than the combined width of the spinal facets making up a facet joint and forming the at least one stabilizer so that it has a width which is sized to make a press fit into the gap between the spinal facets making up a facet joint.

Further method steps include the steps of deploying the spinal facet fusion implant in the facet joint so that the elongated body is simultaneously positioned within both of the facets of the facet joint and so that the at least one stabilizer is positioned within the gap between the spinal facets and maintaining the spinal facet fusion implant in such position while fusion occurs.

In another embodiment, a spinal facet fusion implant includes an elongated body having a distal end, a proximal end and a longitudinal axis extending between the distal end and the proximal end, the elongated body having a cross-sectional profile which is characterized by a primary axis and a secondary axis.

The elongated body has a length along the primary axis which is less than the combined width of the spinal facets making up a facet joint and the cross-sectional profile is non-circular.

In yet another embodiment, a method for fusing a spinal facet joint includes the steps of providing a spinal facet fusion implant having an elongated body having a distal end, a proximal end and a longitudinal axis extending between the distal end and the proximal end, the elongated body having a cross-sectional profile which is characterized by a primary axis and a secondary axis and forming the elongated body so that it has a length along the primary axis which is less than the combined width of the spinal facets making up a facet joint and further providing a non-circular cross-sectional profile.

Further steps include deploying the spinal facet fusion implant in the facet joint so that the elongated body is simultaneously positioned within both of the facets of the facet joint and maintaining the spinal facet fusion implant in such position while fusion occurs.

In still another embodiment, a joint fusion implant includes an elongated body having a distal end, a proximal end and a longitudinal axis extending between the distal end and the proximal end, the elongated body having a cross-sectional profile characterized by a primary axis and a secondary axis and at least one stabilizer extending radially outwardly from the elongated body in the secondary axis.

The elongated body has a length along the primary axis which is less than the combined width of the bones making up the joint and the at least one stabilizer has a width which is sized to make a press fit into the gap between the bones making up the joint.

In another embodiment, a method for fusing a joint includes the steps of providing a fusion implant that includes an elongated body having a distal end, a proximal end and a longitudinal axis extending between the distal end and the proximal end, the elongated body having a cross-sectional profile characterized by a primary axis and a secondary axis and at least one stabilizer extending radially outwardly from the elongated body in the secondary axis.

Further steps include forming the elongated body so that it has a length along the primary axis which is less than the combined width of the bones making up the joint and forming the at least one stabilizer so that it has a width which is sized to make a press fit into the gap between the bones making up the joint.

Still further steps include deploying the fusion implant in the joint so that the elongated body is simultaneously positioned within both of the bones of the joint and the at least one stabilizer is positioned within the gap between the bones and maintaining the fusion implant in such position while fusion occurs.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 1C is a side elevational view thereof;

FIG. 3C is an end elevational view thereof;

FIG. 4B is an end elevational view thereof;

FIG. 4C is a top plan view thereof;

FIG. 5A is a perspective view of an implant having a hex shape and no fins;

FIG. 5B is a side elevational view thereof;

FIG. 6D is an end elevational view thereof;

FIG. 7B is a side elevational view thereof;

FIG. 8A is a diagrammatic top plan view of a superior and an inferior facet joint and a drilled bore or cavity formed in said facet joints, said cavity receiving a tapered implant;

FIG. 11 is a perspective view of the novel directional cannula;

FIG. 12 is a perspective view of the novel facet distractor;

FIG. 13 is a perspective view of the novel guide pin;

FIG. 23B is a transverse cross-sectional view of said second embodiment of said directional cannula;

DETAILED DESCRIPTION OF THE PREFERRED EMBODIMENT

Figure 1A:
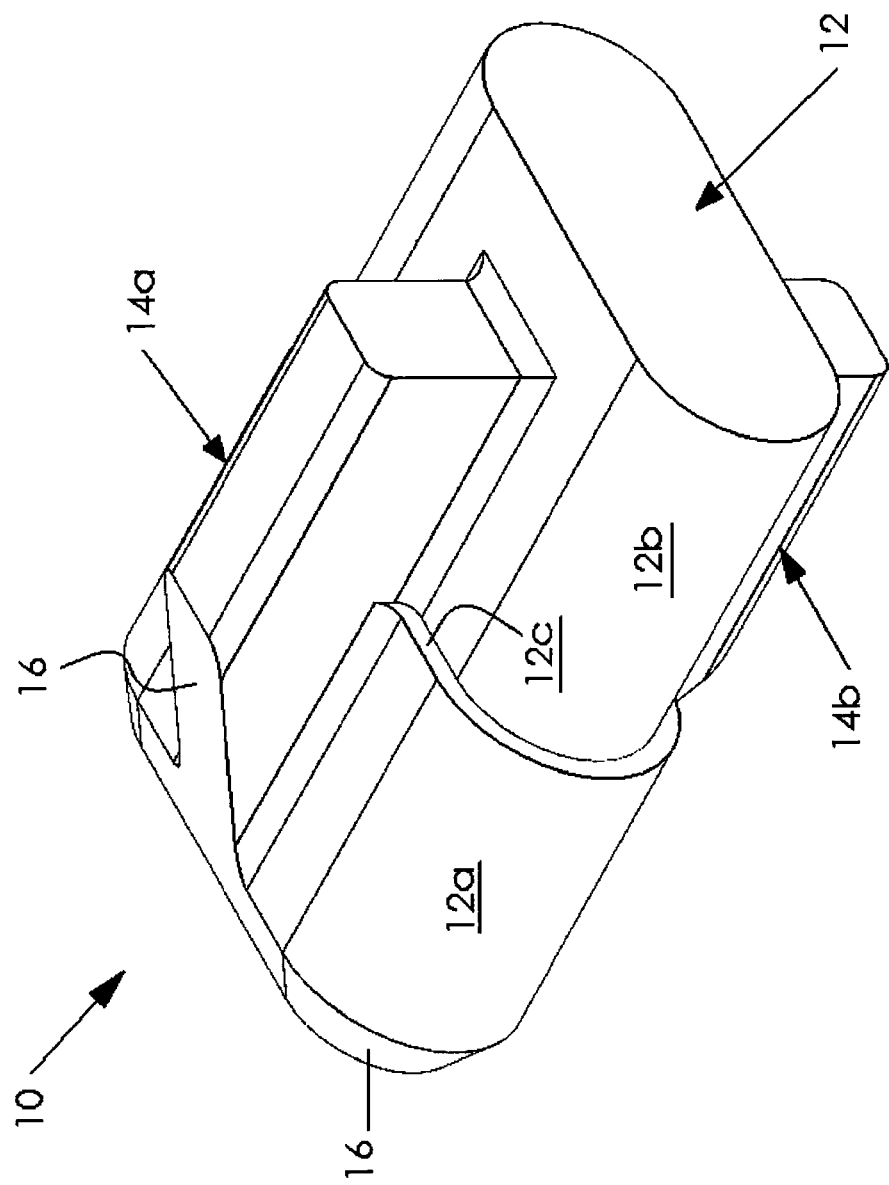
FIG. 1A is a perspective view of a fusion implant having a stepped main body and fins.
Figure 1B:
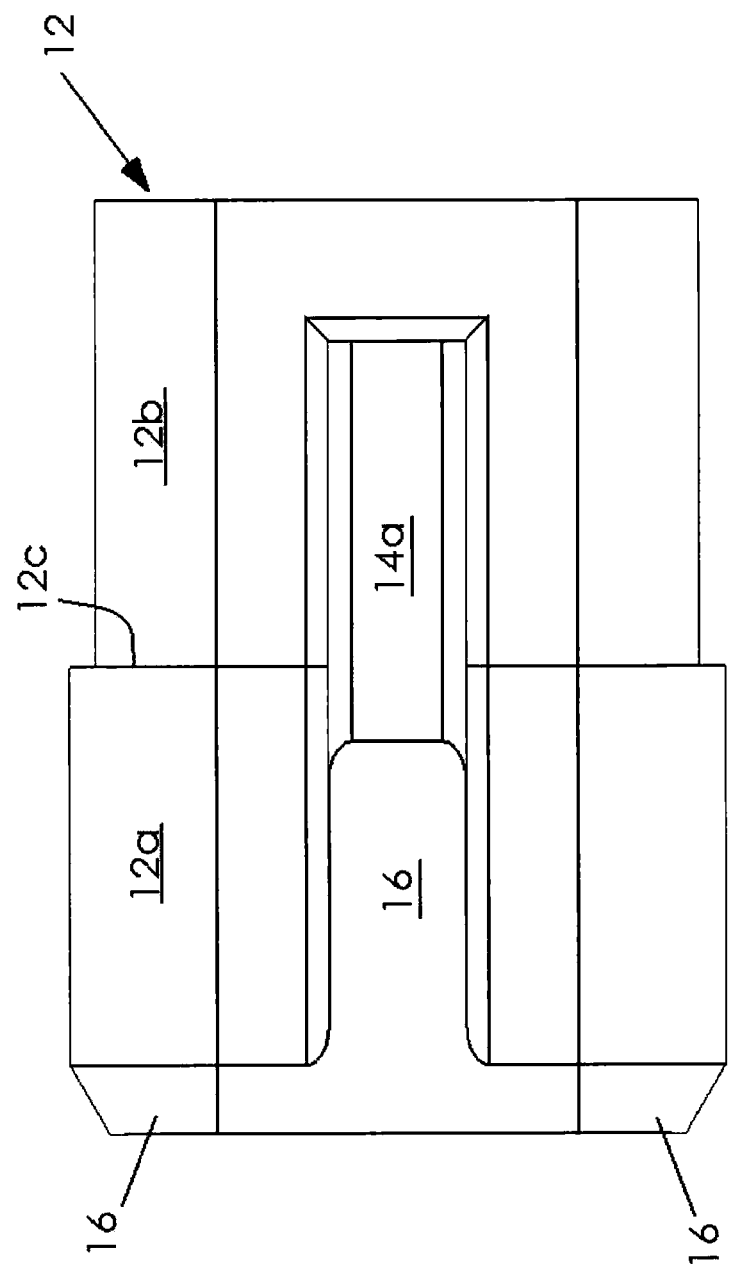
FIG. 1B is a top plan view thereof.

Referring now to FIGS. 1A-C, the novel spinal facet fusion implant is denoted 10 as a whole. Fusion implant 10 includes main body 12 and at least one stabilizer fin 14. The illustrated embodiment includes first stabilizer fin 14a and second stabilizer fin 14b.

Body 10 is an elongated element having structural integrity. The distal end of main body 12 and the distal end of stabilizers 14a, 14b are chamfered as at 16 to facilitate insertion of fusion implant 10 into the facet joint as disclosed hereinafter. Body 12 preferably has a rounded rectangular cross-section, an ovoid cross-section, a laterally-extended cross-section, or some other non-round cross-section to inhibit rotation of main body 12 about a longitudinal center axis.

Fusion implant 10 is intended to be inserted into a facet joint using a posterior approach. The posterior approach is familiar to spine surgeons, thereby providing an increased level of comfort for the surgeon, and also minimizing the possibility of damage to the spinal cord during fusion implant insertion.

Stabilizer fins 14a, 14b are received in a gap located between opposing facet surfaces to prevent rotation of fusion implant 10 within the facet joint. Stabilizers 14a is formed in and extends along the upper surface of main body 12 and stabilizer 14b is formed in and extends along the lower surface of main body 12. Stabilizers 14a, 14b preferably have a width just slightly larger than the gap between the opposing articular surfaces of a facet joint so that the stabilizers fit snugly therebetween.

The distal end 12a of main body 12a has a greater thickness than proximal end 12b of said main body, there being transversely disposed step 12c therebetween. The greater thickness of said distal end supports the load for a long period of time. If said distal end 12a of main body 12 is eventually crushed, it becomes flush with proximal end 12b and fusion implant 10 continues to perform its function.

Figure 2A:
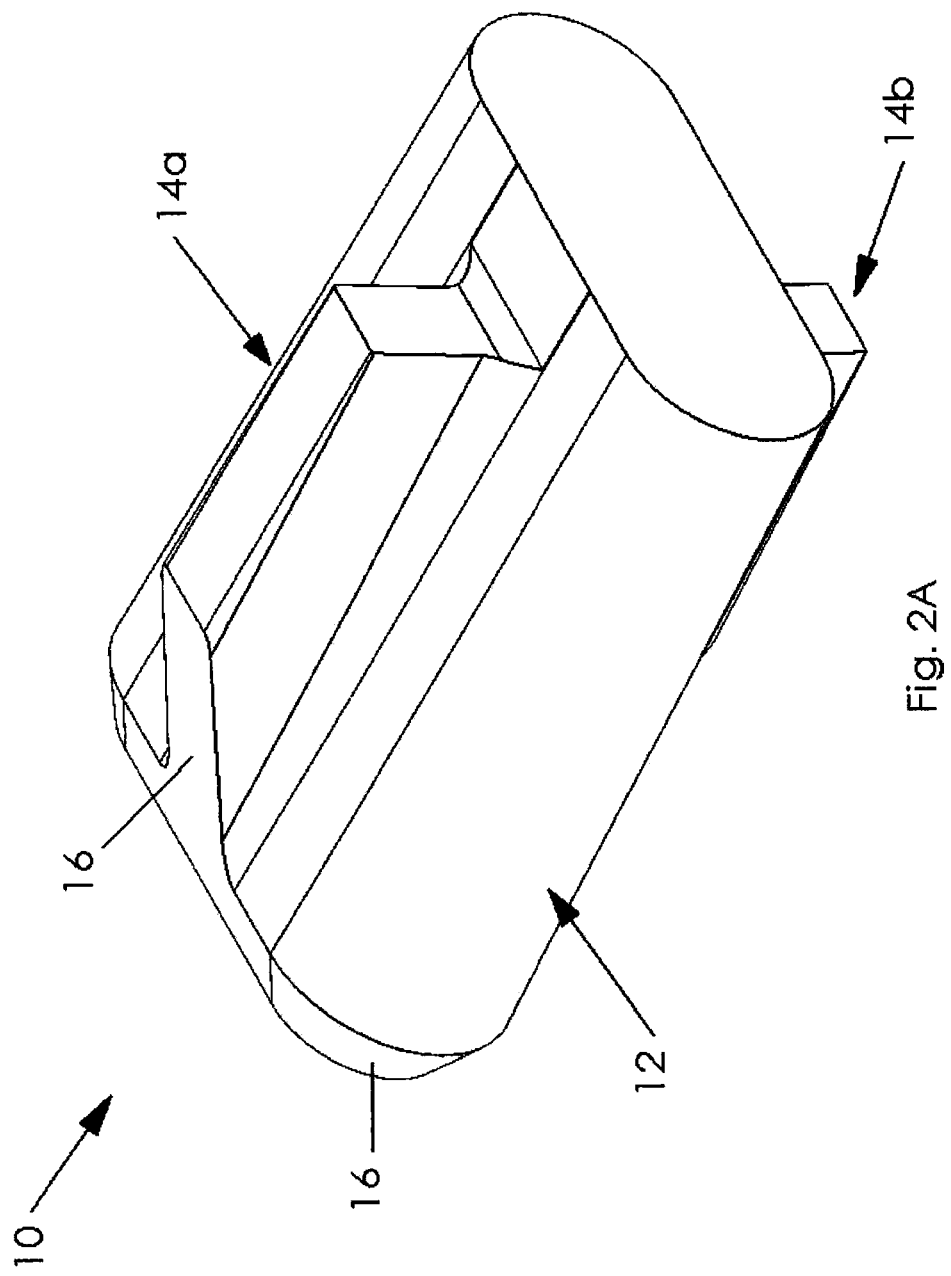
FIG. 2A is a perspective view of a fusion implant main body having fins and a greater thickness on the distal end relative to the proximal end.
Figure 2B:
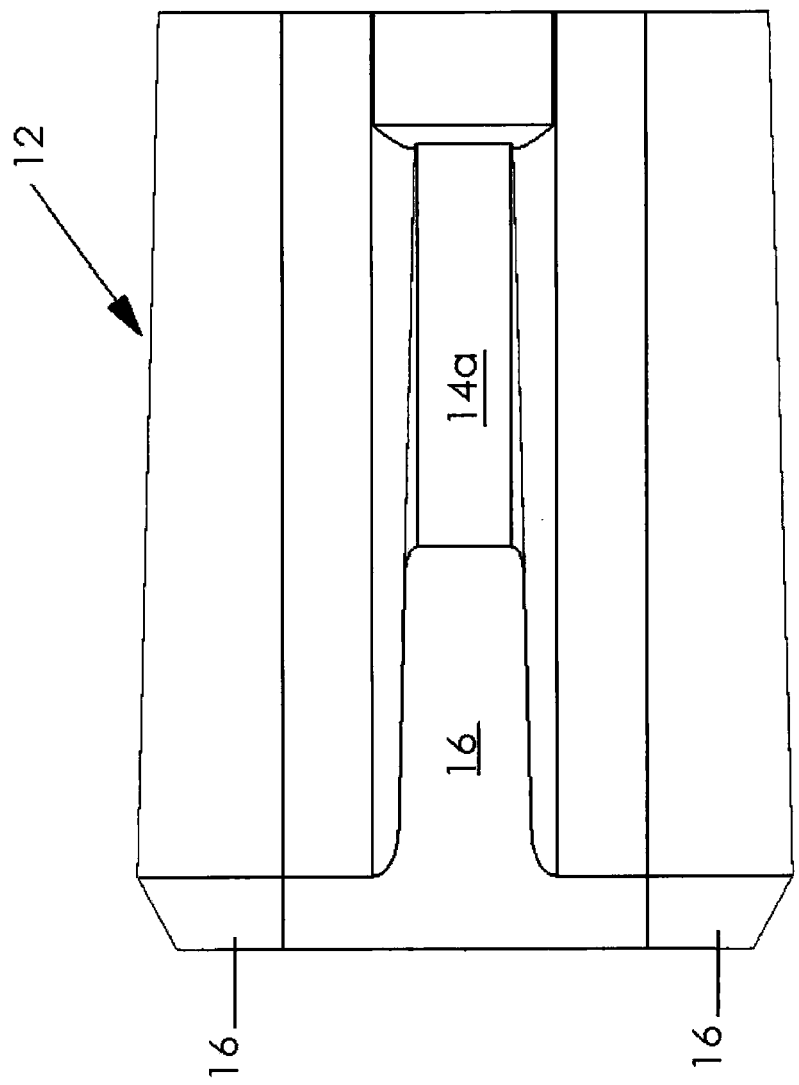
FIG. 2B is a top plan view thereof.
Figure 2C:
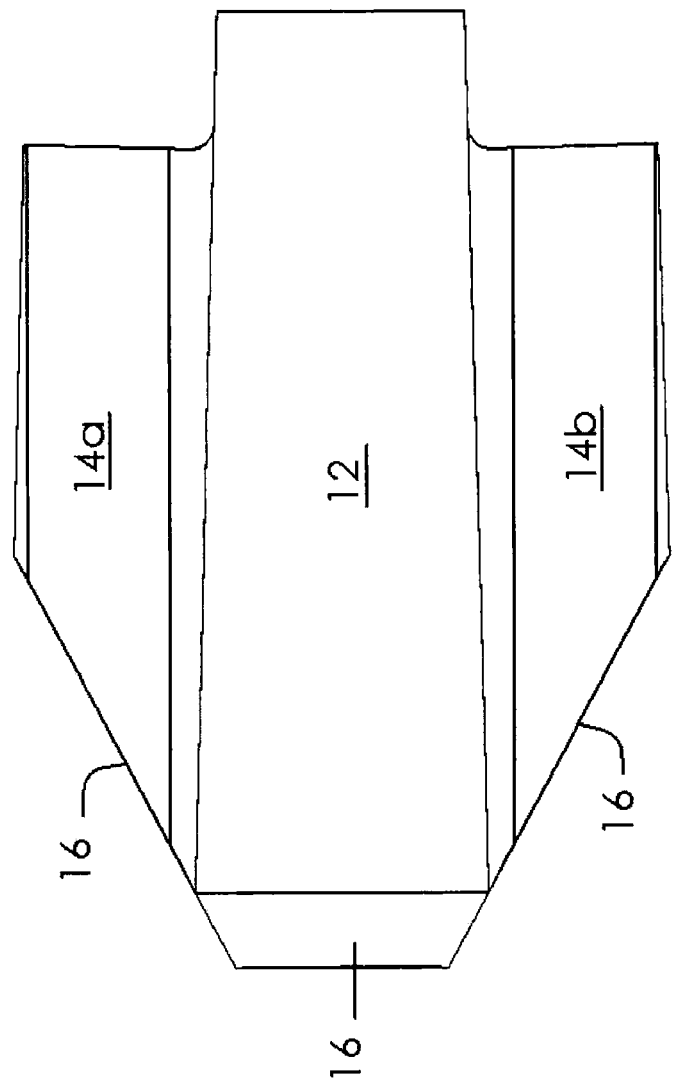
FIG. 2C is a side elevational view thereof.

The embodiment of FIGS. 2A-C has an inverse taper formed in main body 12 and in stabilizer fins 14a, 14b to prevent migration of implant 10. As perhaps best understood in connection with FIG. 2B, fin 14a is wider at its distal end than at its proximal end; fin 14b has the same structure. This wedge shape prevents distal-to-proximal travel of implant 10. This eliminates the need for teeth that perform the same function.

Figure 3A:
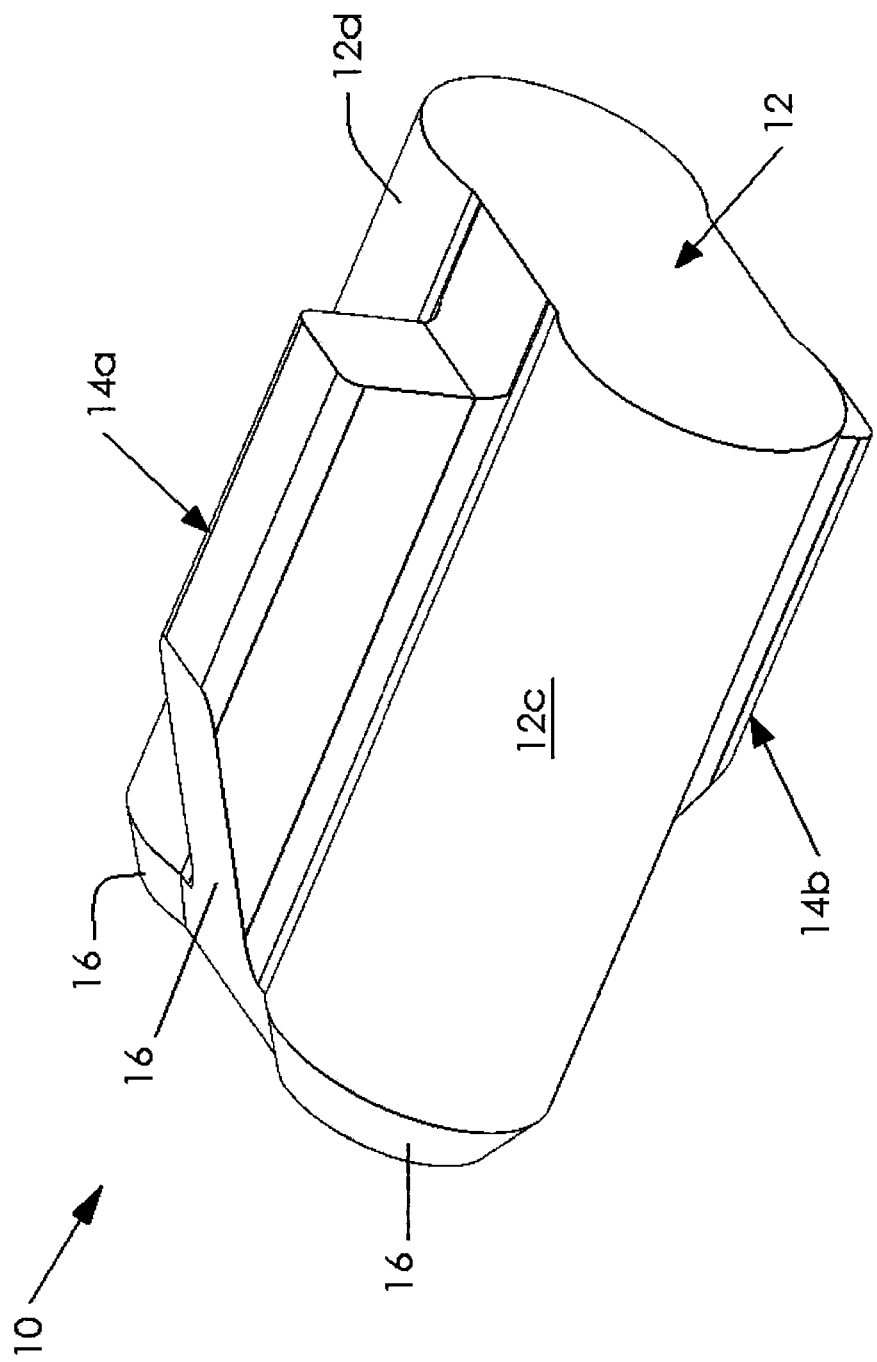
FIG. 3A is a perspective view of a fusion implant having a main body with bulbous parts and fins.
Figure 3B:
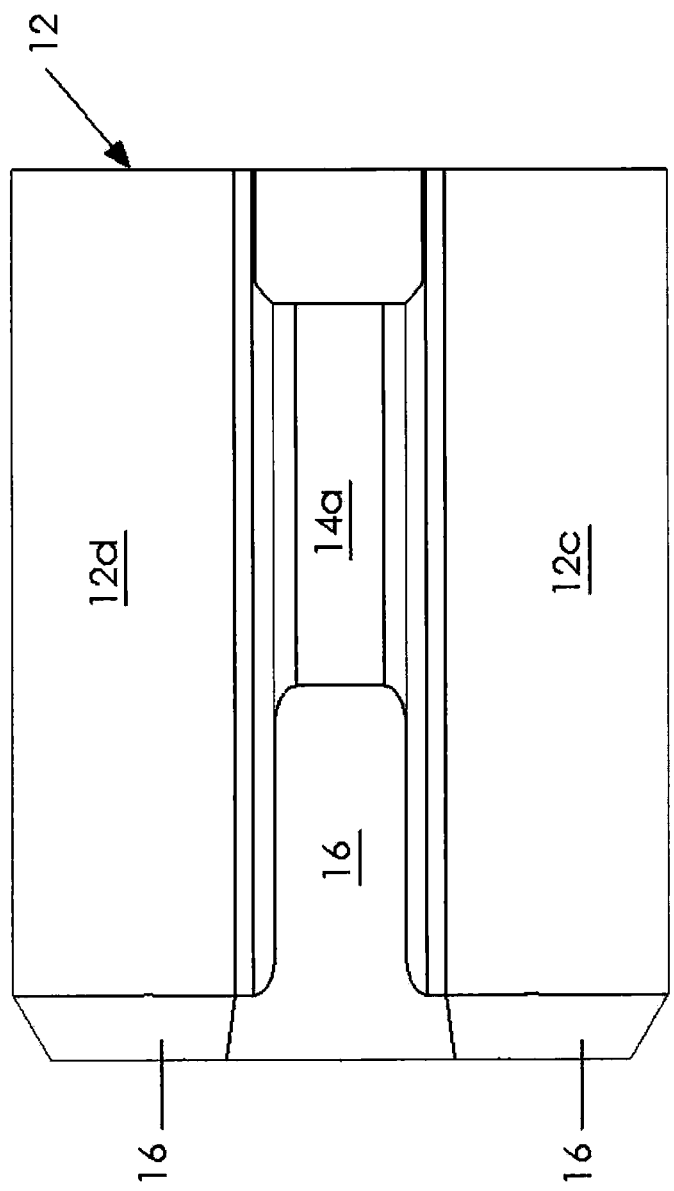
FIG. 3B is a top plan view thereof.
Figure 4A:
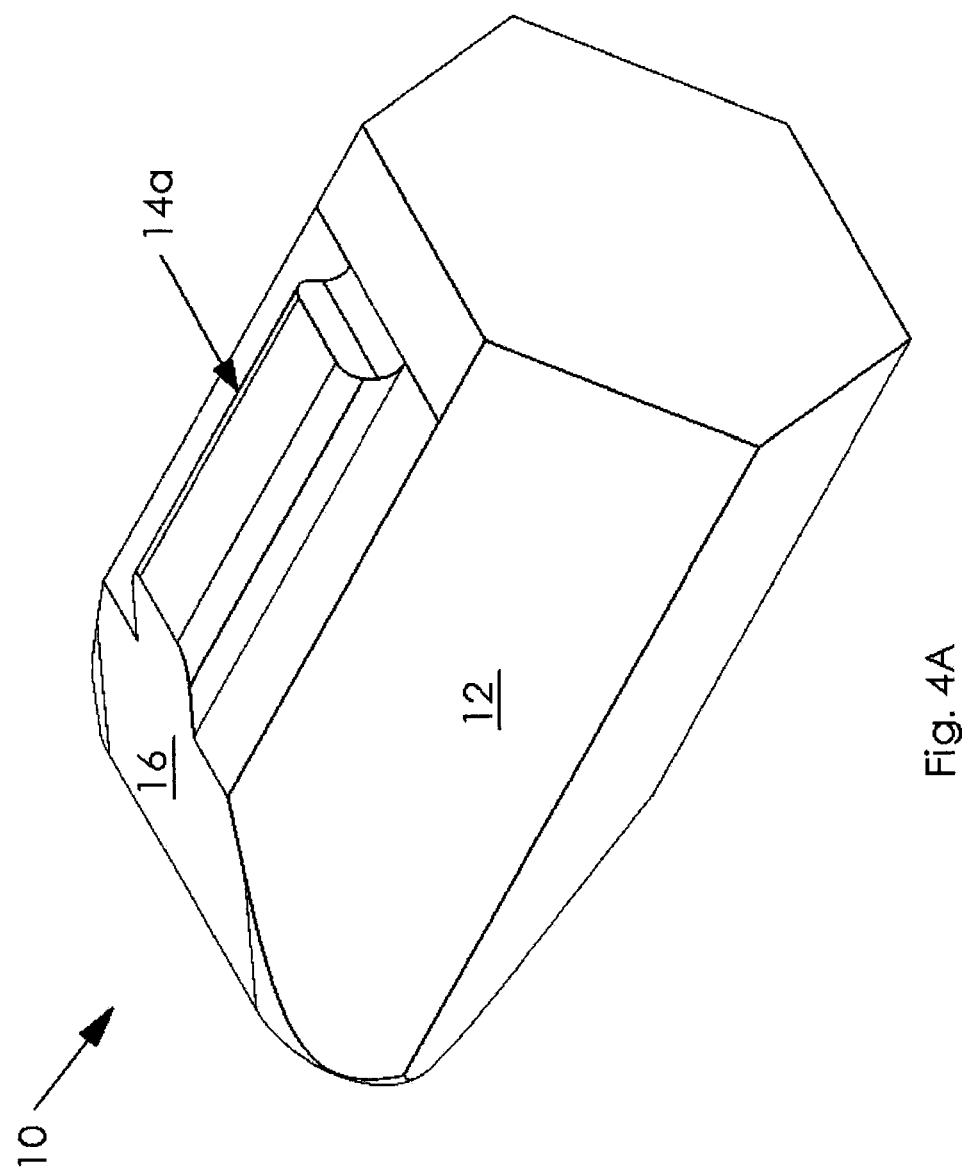
FIG. 4A is a perspective view of an implant having a hex shape and at least one stabilizing fin.
Figure 4D:
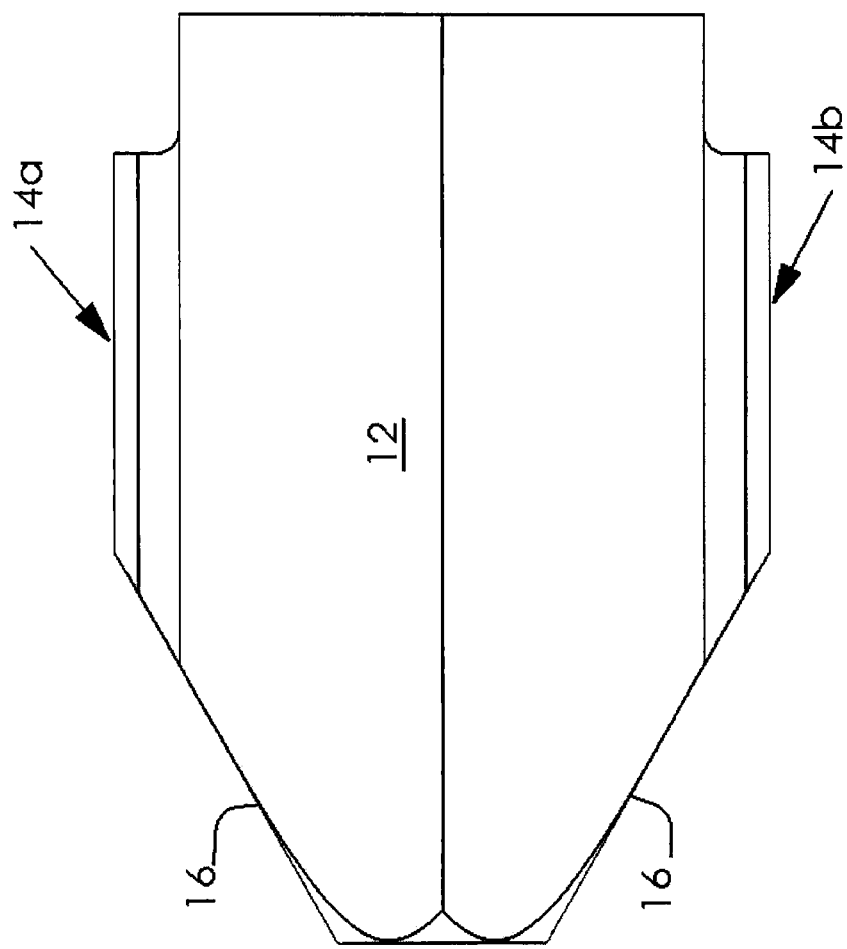
FIG. 4D is a side elevational view thereof.

The embodiment of FIG. 3A differs from the embodiment of FIGS. 2A-C in that main body 12 is bulbous on its left and right sides as depicted. It is sometimes referred to as a figure eight main body in view of said bulbosities. The bulbosities are denoted 12c and 12d. They serve the same function as raised area 12a in the embodiment of FIGS. 1A-C in that if they are crushed over time until they are flush with the non-bulbous central region of main body 12, said main body will still remain firmly and functionally positioned in the facet joint. Without the raised area or the bulbosities, crushing of main body 12 over time would loosen it relative to its facet joint.

FIGS. 4A-D depict an embodiment characterized by main body 12 that is hexagonal in transverse section as depicted. Stabilizer fins 14, 14b may also be shorter in radial extent in this embodiment. This shape helps prevent rotation of implant 10.

Figure 5C:
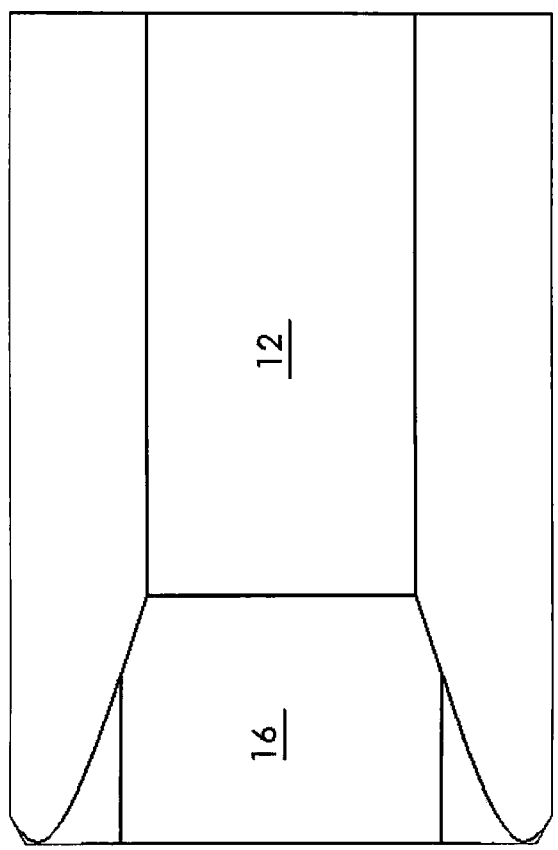
FIG. 5C is a top plan view thereof.
Figure 6A:
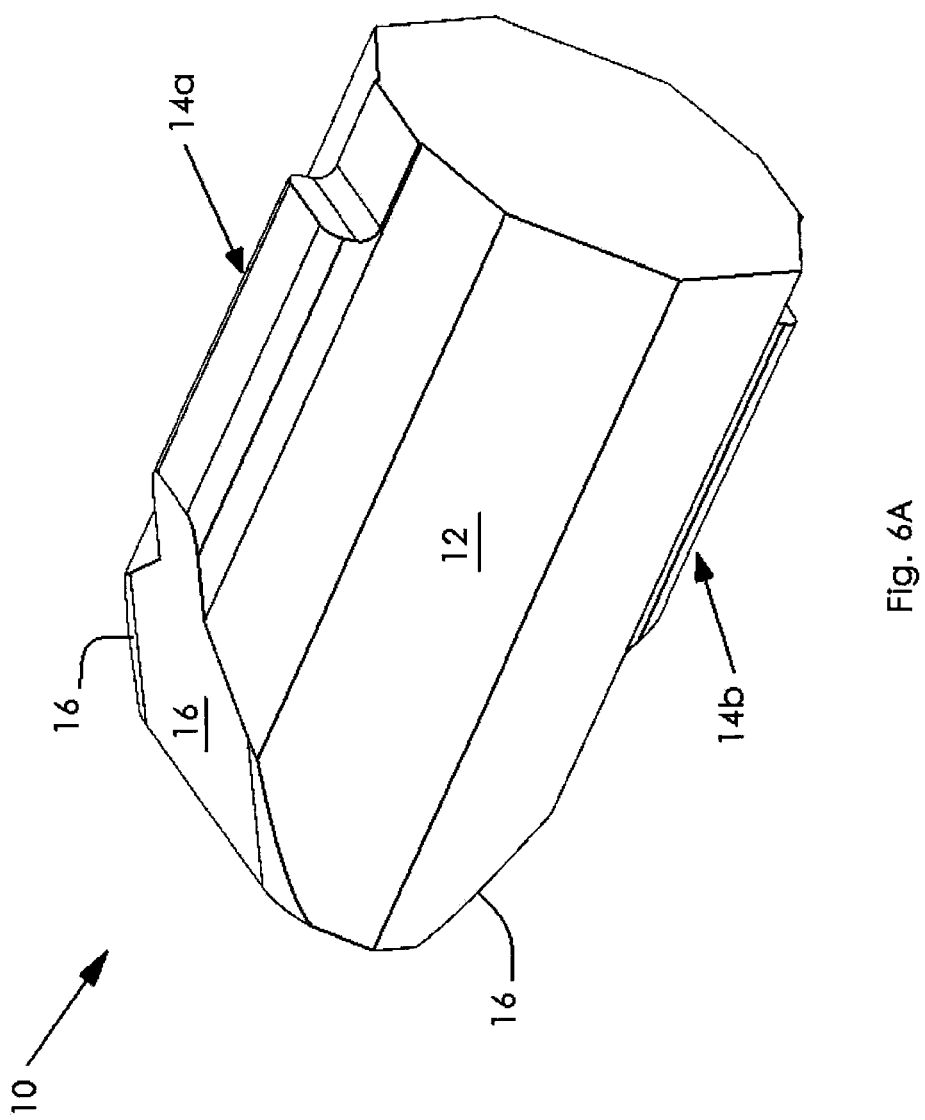
FIG. 6A is a perspective view of an implant having a polygonal shape in transverse section and at least one stabilizing fin.
Figure 6B:
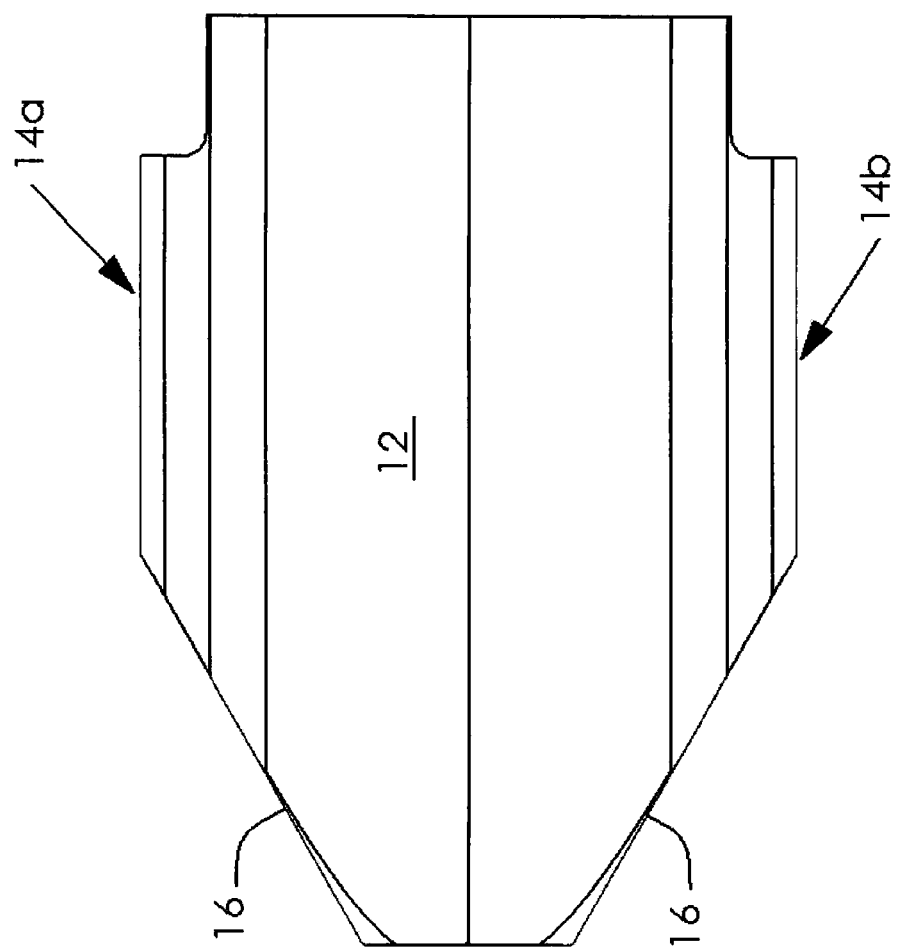
FIG. 6B is a side elevational view thereof.
Figure 6C:
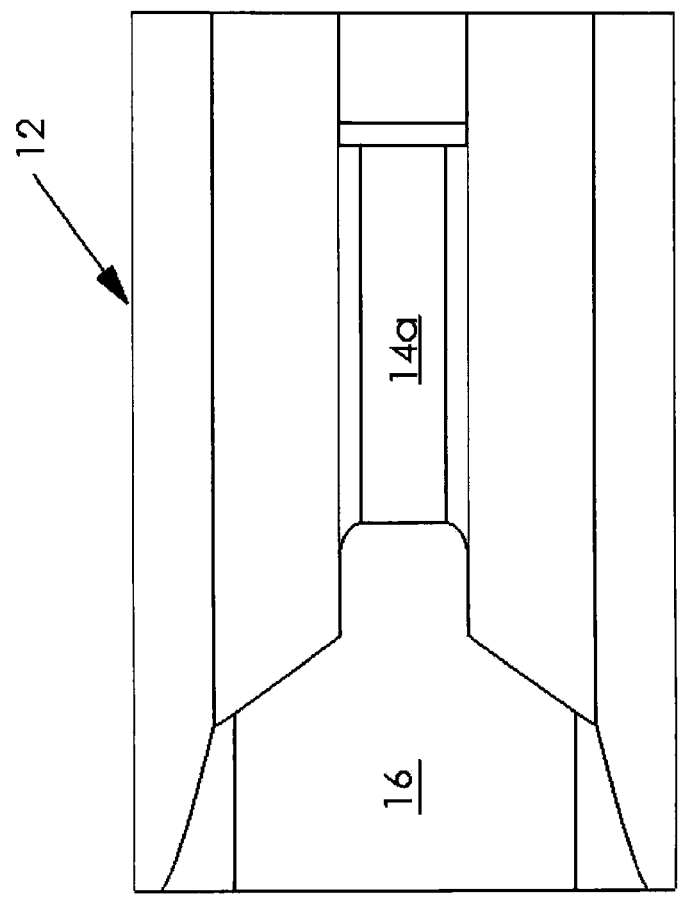
FIG. 6C is a top plan view thereof.

The embodiment of FIGS. 5A-C differs from the embodiment of FIGS. 4A-D in that the embodiment of FIGS. 5A-C is not provided with stabilizer fins 14a, 14b.

FIGS. 6A-D depict an embodiment of implant 10 having a polygonal main body 12 and stabilizer fins 14a, 14b of truncate radial extent.

Figure 7A:
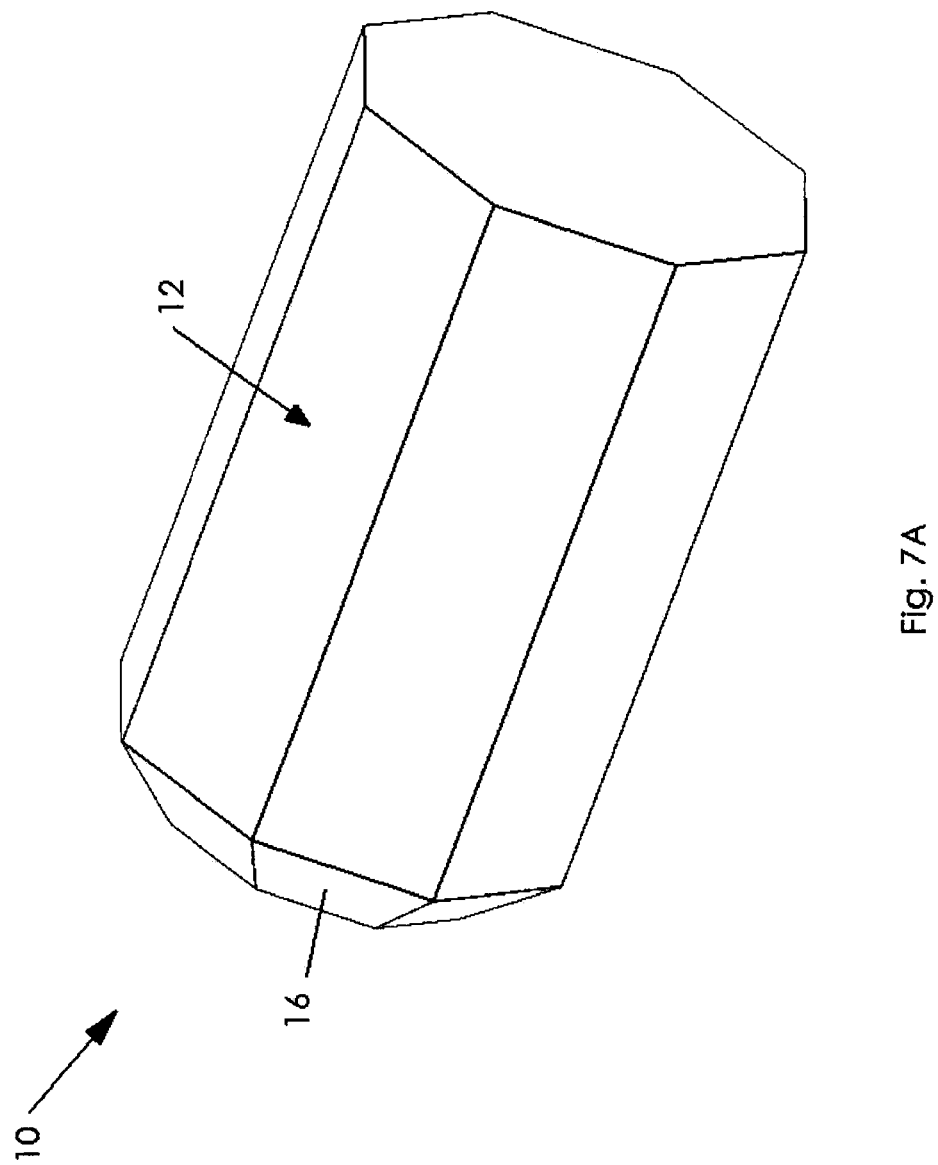
FIG. 7A is a perspective view of an implant having an octagonal main body and no fins.

The embodiment of FIGS. 7A-B has main body 12 of polygonal configuration and no stabilizer fins.

Referring now to FIGS. 8A-D, an instrument is first used to determine the vertical plane 18 of the facet joint. Identifying the vertical plane of the facet joint is important because said plane is used to identify the proper position for cavity 20 which is to be formed in the facet joint to receive fusion implant 10. The superior facet is denoted 22a in FIGS. 8-D and the inferior facet is denoted 22b. The inverted tapered cavity depicted in FIGS. 8A-D is intended for use with the inverted tapered implant of FIGS. 2A-C.

A disclosure of the novel tools used with implant 10 follows.

Figure 9:
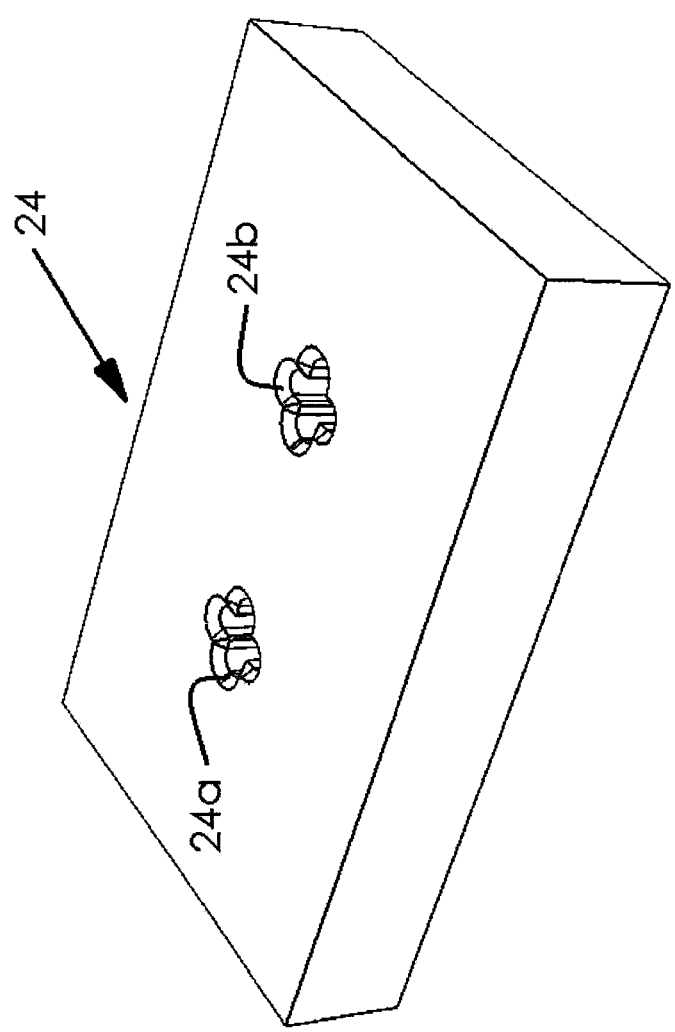
FIG. 9 is a perspective view of the novel implant loading block.

Implant loading block 24 having bores 24a, 24b for slideably receiving implants 10 is depicted in FIG. 9.

Figure 10:
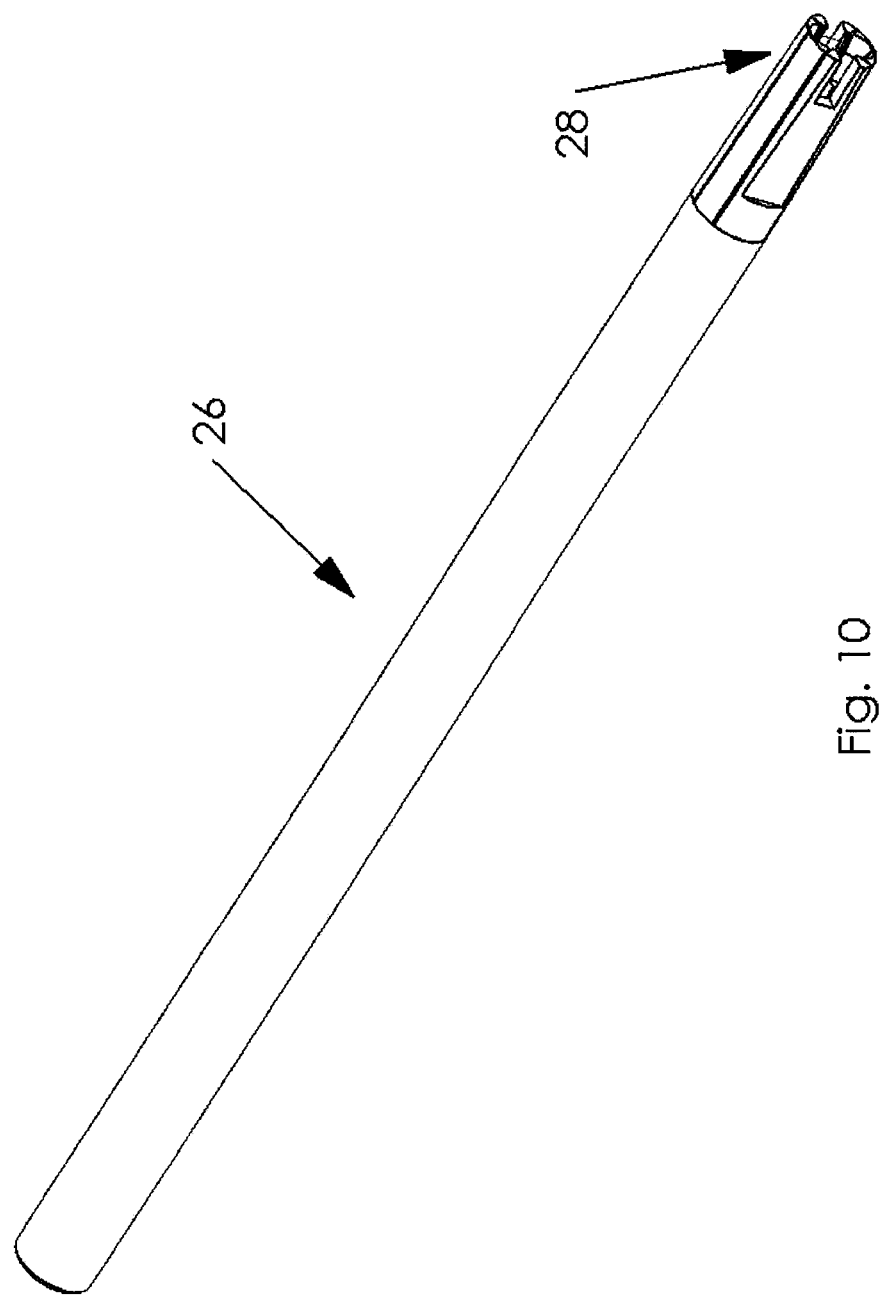
FIG. 10 is a perspective view of the novel implant holder.

Implant holder 26 is depicted in FIG. 10. Leading end 28 includes a plurality of flexible arms 28 that engage an implant 10 to lift it from bore 24a or 24b of implant loading block 24. Implant holder 26 does not have alignment pins. It has flats that align inside directional cannula 30. Drill guide 36, disclosed hereinafter, also has such flats.

Directional cannula 30 having diametrically opposed arms 30a, 30b at its leading or distal end is depicted in FIG. 11. Arms 30a, 30b maintain the direction of the joint to guide the other instruments, and also maintain the distraction of the joint.

FIG. 12 depicts facet distractor 32 having leading end 32a adapted to engage into the facet joint to find the direction of the plane of the facet joint.

Guide pin 34 is depicted in FIG. 13. Its use is optional.

Figure 14A:
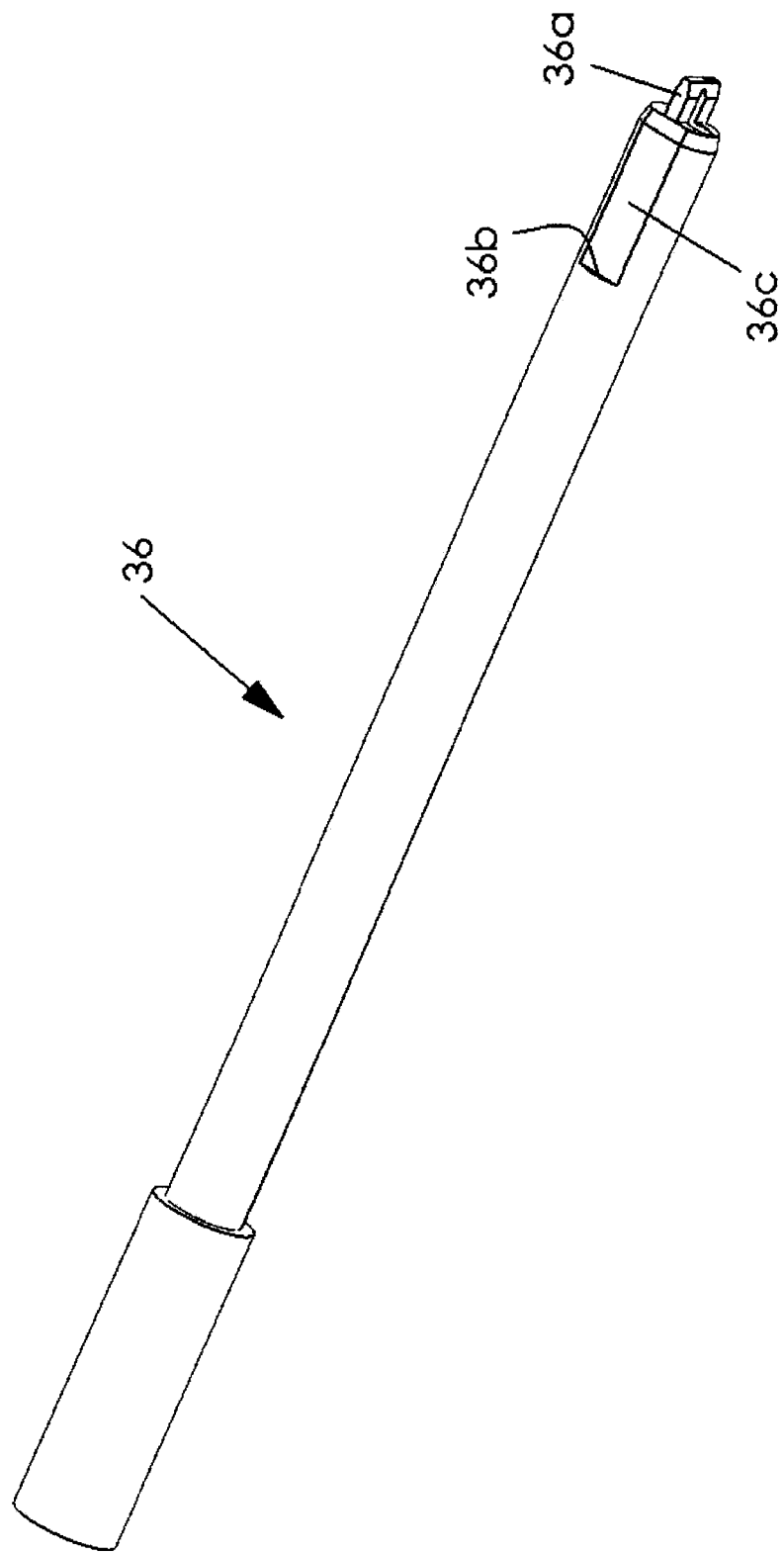
FIG. 14A is a first perspective view of the drill guide and blade.
Figure 14B:
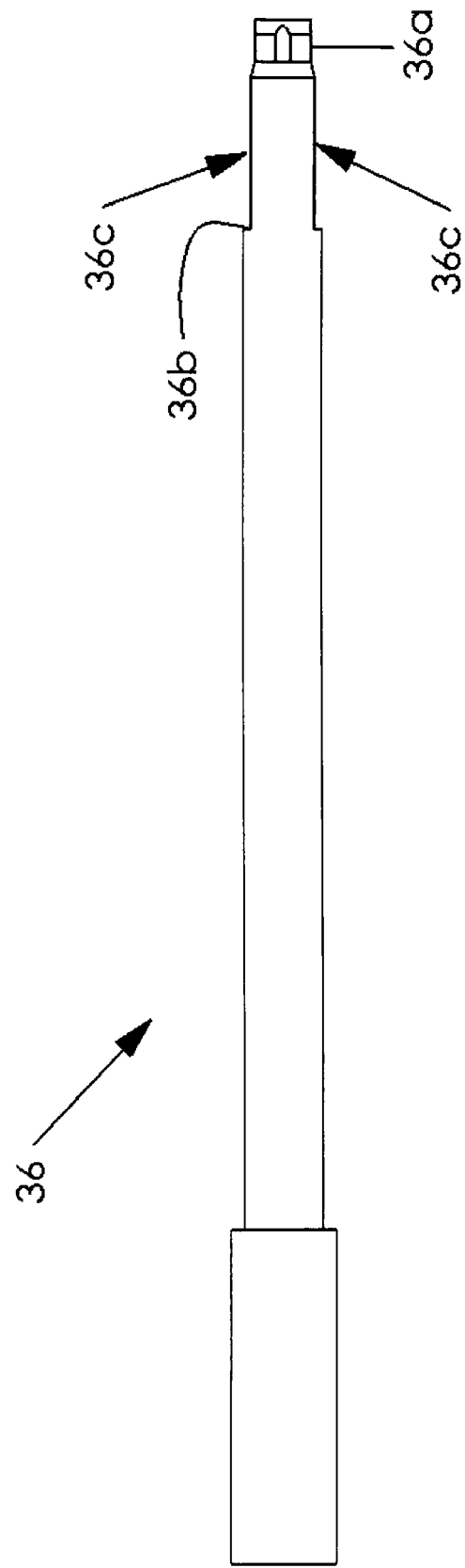
FIG. 14B is a side elevational view thereof.
Figure 14C:
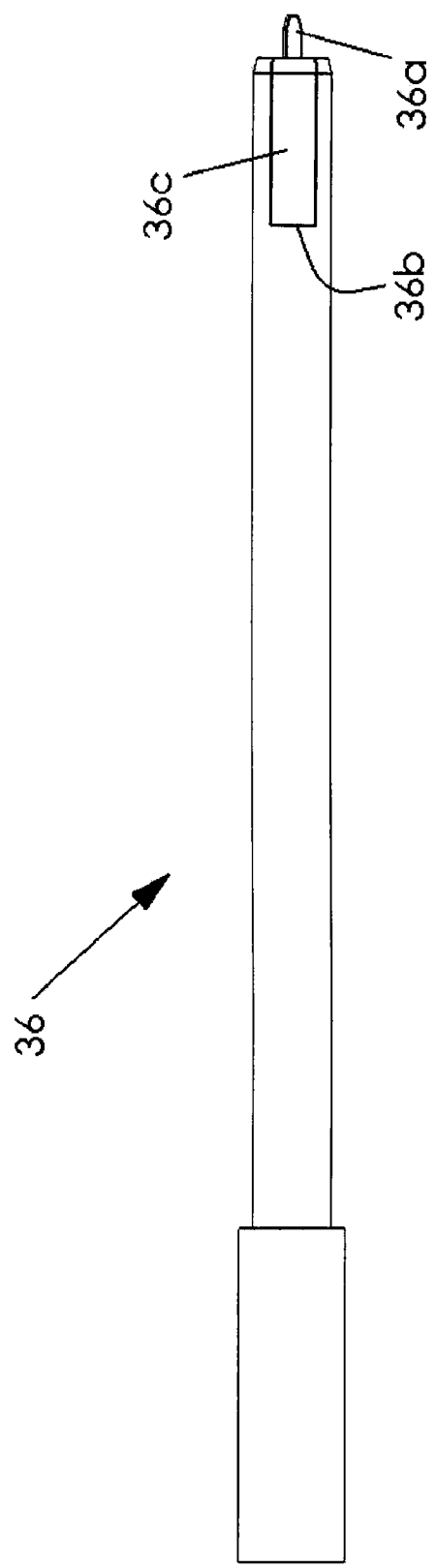
FIG. 14C is a top plan view thereof.
Figure 14D:
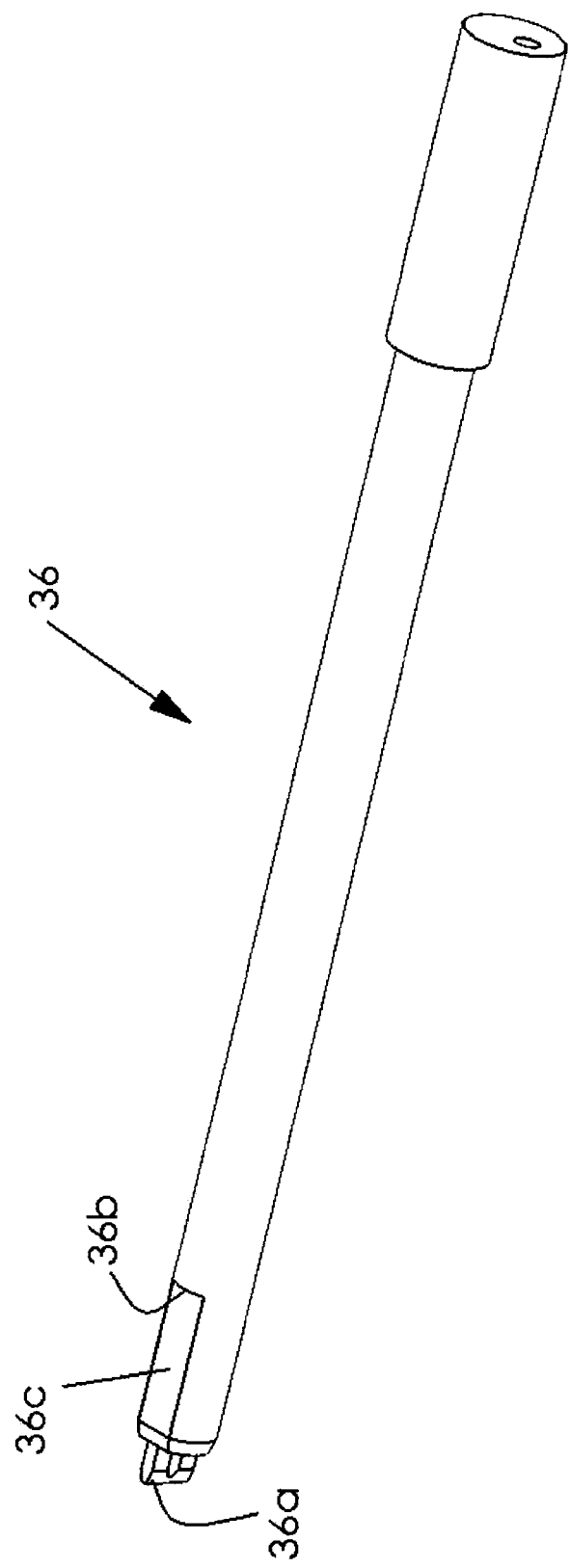
FIG. 14D is a second perspective view thereof.

FIGS. 14A-D depict drill guide 36 having blade 36a, positive stop 36b, and alignment flats 36c. FIG. 14A is a first perspective view, FIG. 14B provides a side elevational view, FIG. 14C provides a top plan view and FIG. 14D provides a second perspective view. Drill guide 36 stabilizes the drill bit during the drilling procedure.

Figure 15A:
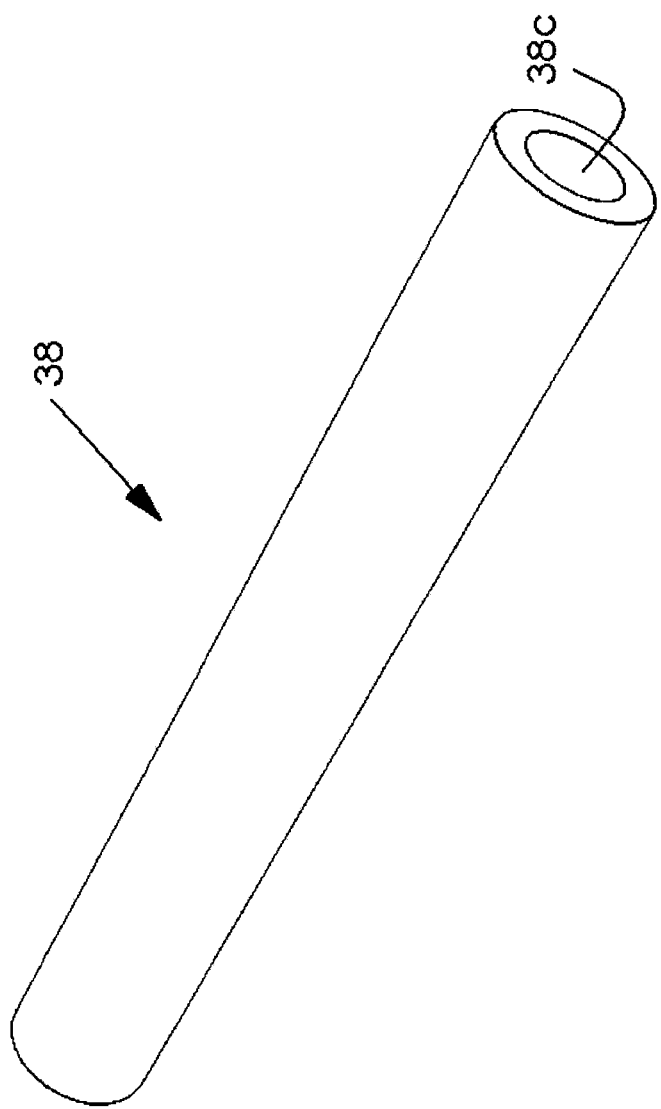
FIG. 15A is a perspective view of a tapping cap.
Figure 15B:
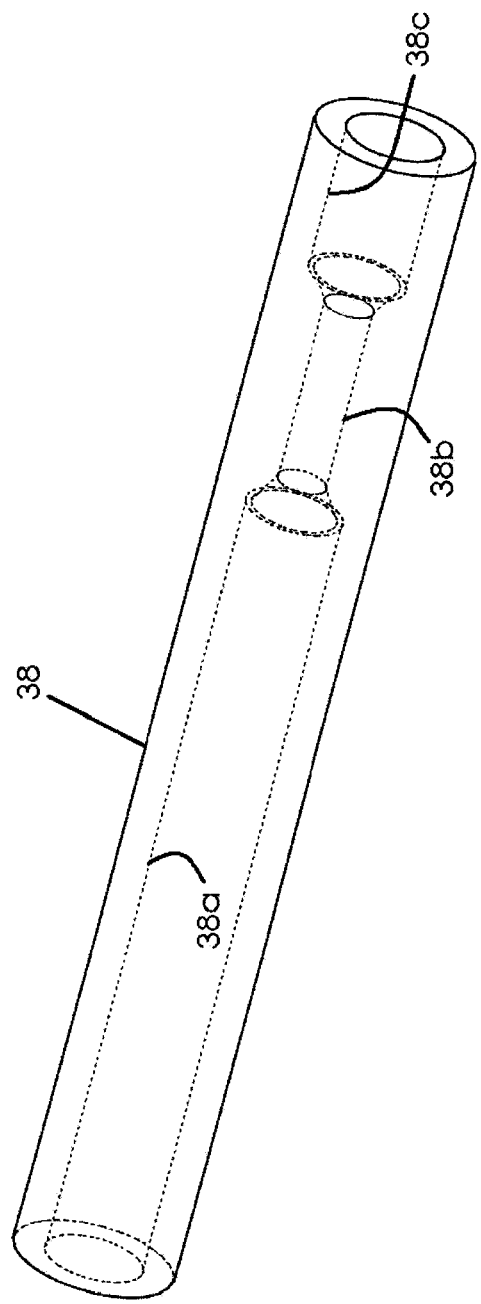
FIG. 15B is a perspective view thereof as in FIG. 15A and further including dotted lines to indicate hidden structure.
Figure 15C:
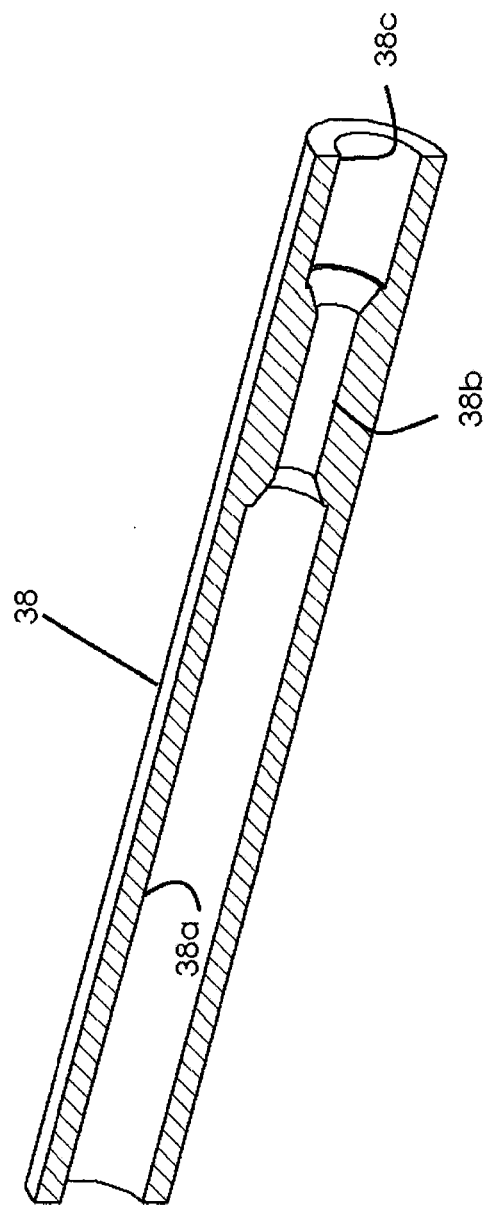
FIG. 15C is a longitudinal sectional view of the structure depicted in FIGS. 15A and 15B.

FIGS. 15A-C respectively depict tapping cap 38 in perspective, perspective with dotted lines to indicate hidden structure, and in longitudinal section to also reveal hidden structure. Distal bore 38a of tapping cap 38 is used to tap directional cannula 30 into its functional position and proximal bore 38c is used to tap facet distractor 32 into its functional positional. The diameter of distal bore 38a reduces down to medial bore 38b and proximal bore 38c has the same diameter as distal bore 38a. Medial bore 38b allows guide pin 34 to slide through.

Figure 16A:
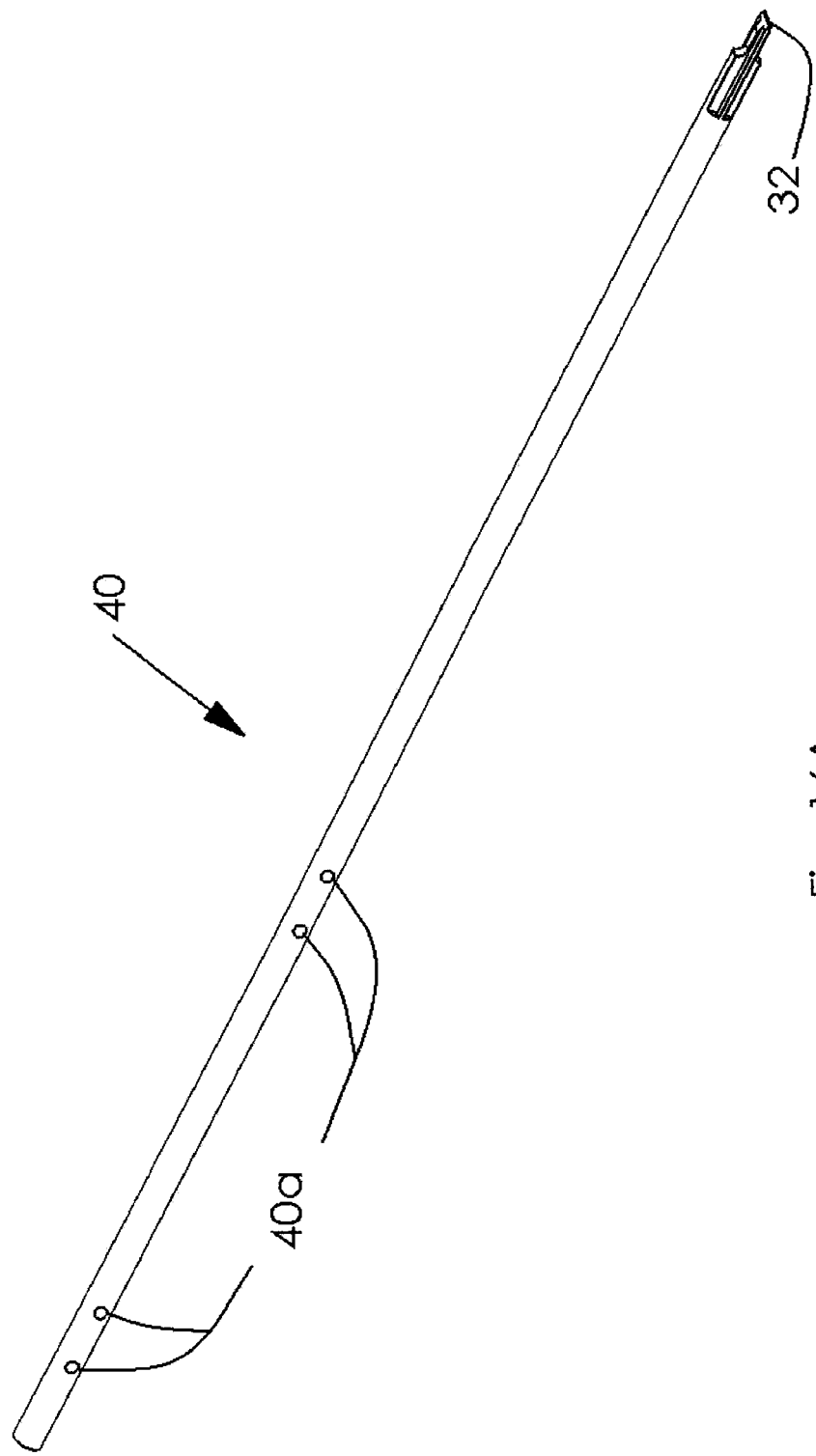
FIG. 16A is a perspective view of the one step facet distractor and implant holder with the facet distractor ensleeved within the lumen of the implant holder.
Figure 16B:
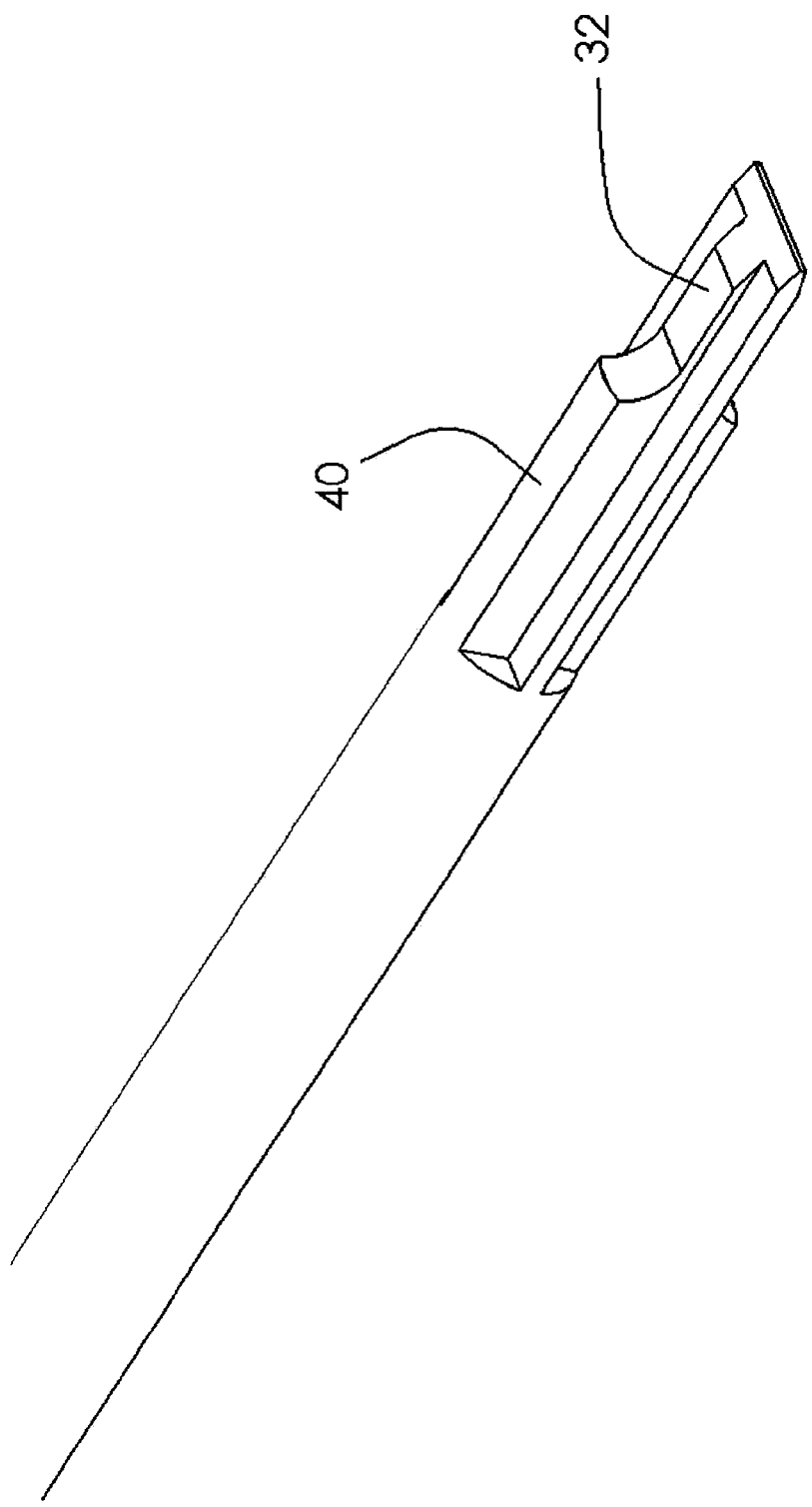
FIG. 16B is an enlarged view of the distal end of the facet distractor and implant holder of FIG. 16A.

FIGS. 16A and 16B depict one step facet distractor 32 when it is received within the lumen of implant holder 40 which is a second embodiment of implant holder 26. FIG. 16B depicts the tip of facet distractor 32 and implant holder 40 in enlarged detail. Implant Holder 40 does not need alignment pins 40a because the orientation is fixed relative to facet distractor 32.

Figure 17:
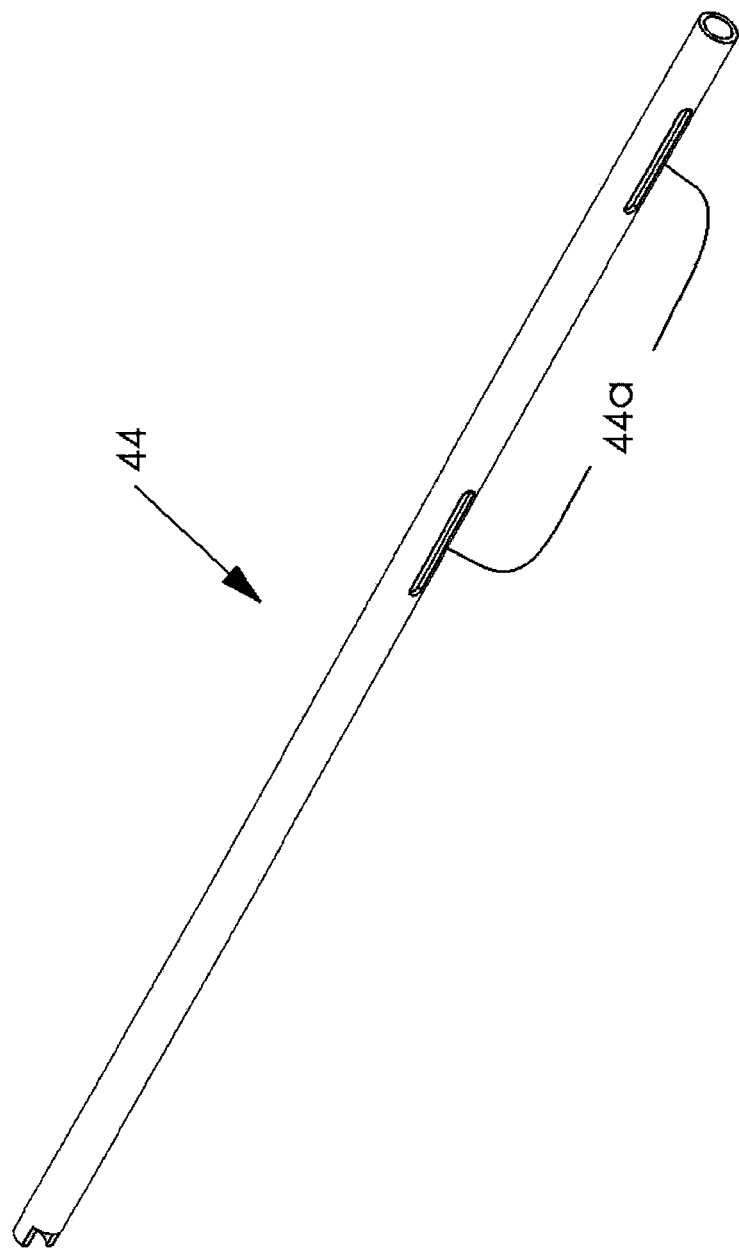
FIG. 17 is a perspective view of the one step sleeve or implant tamp.
Figure 18:
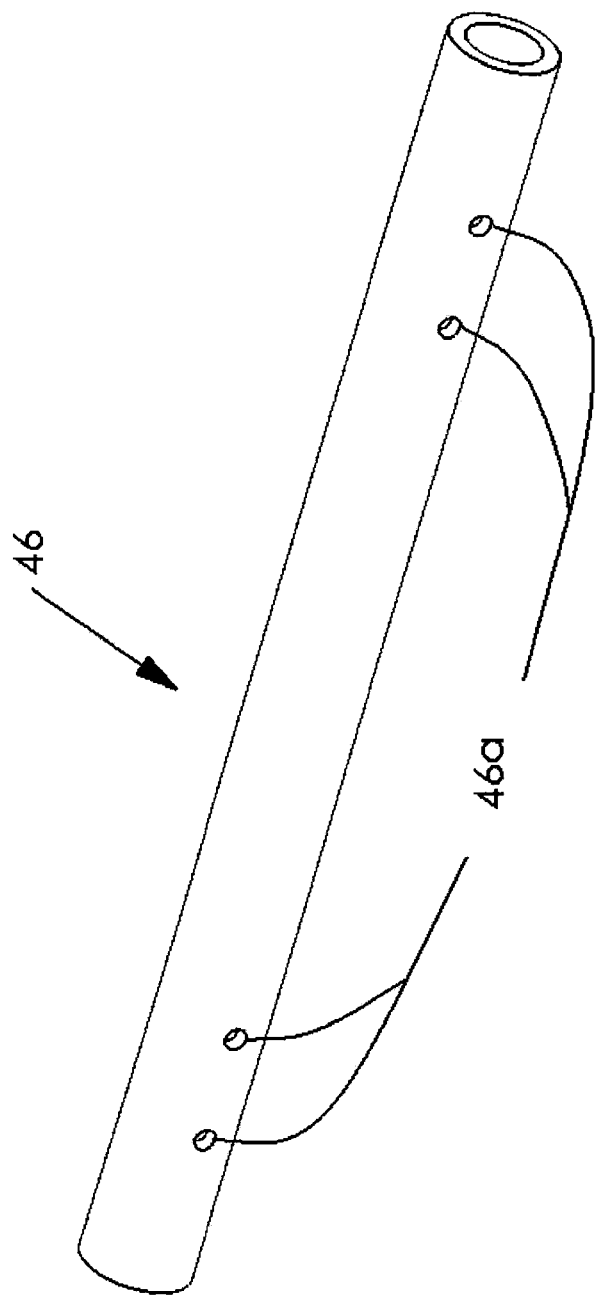
FIG. 18 is a perspective view of the one step handle.

FIG. 17 depicts implant tamp 44 that is used to drive a hollow implant 10 into its functional position. Slots 44a allow implant tamp 44 to slide a predetermined distance as disclosed hereinafter FIG. 18 depicts one step holder 46 having openings collectively denoted 46a that holds the complete instrument assembly while implant 10 is being tapped into its functional position The four pins, collectively denoted 41 in FIG. 16A, are used in the assembly of implant tamp 44 and handle 46. The instrument as assembled includes facet distractor 32 which is ensleeved within the lumen of implant holder 26, which is in turn ensleeved within the lumen of implant tamp 44, which is in turn ensleeved within the lumen of handle 46. More particularly, pins 26a extend sequentially through their associated slots 44a and into their associated opening 46a formed in handle 46.

Figure 19:
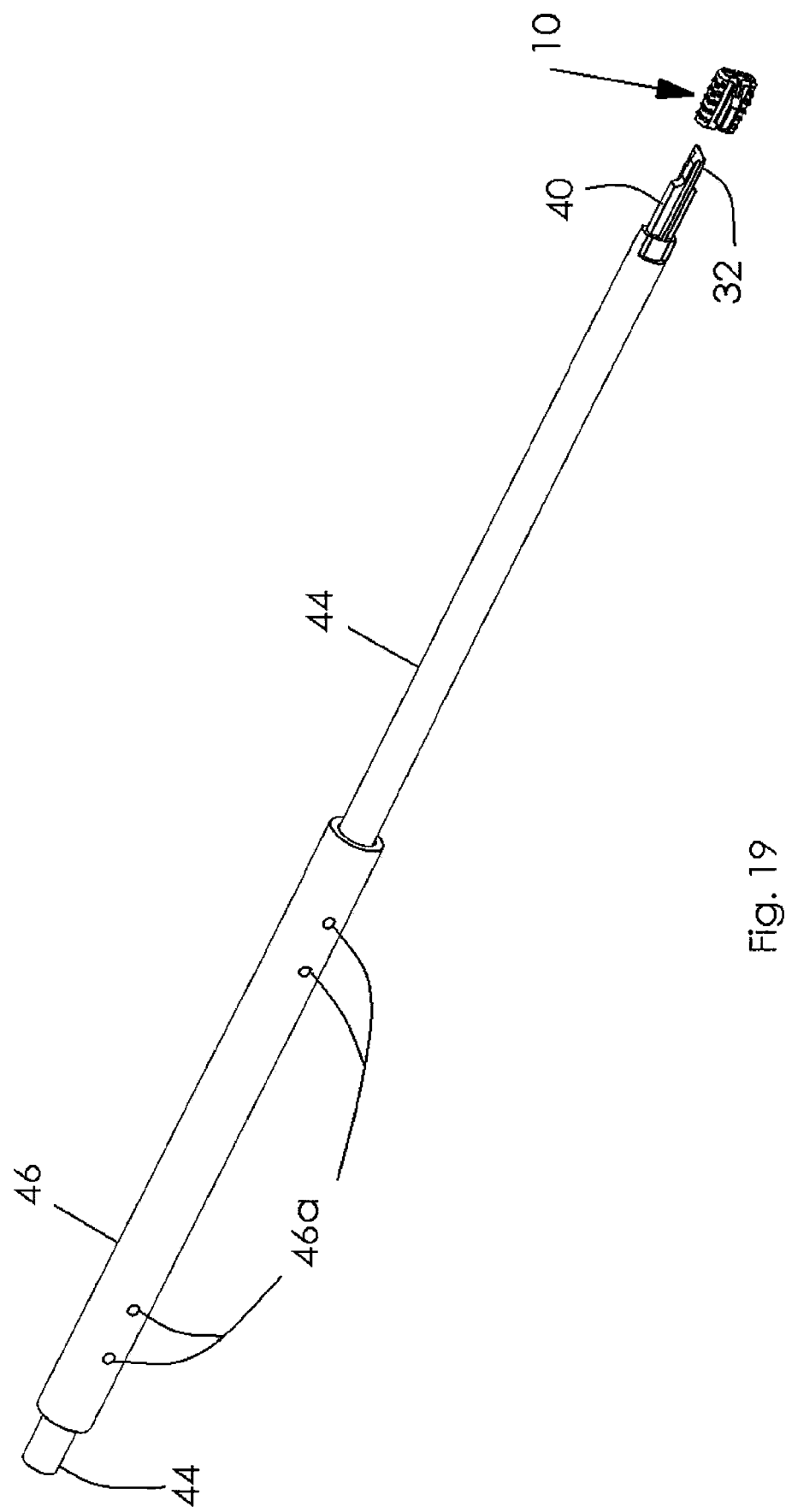
FIG. 19 is an exploded perspective view of the one step assembly with implant before the implant is loaded onto the facet distractor.

FIG. 19 depicts facet distractor 32, implant holder 26, implant tamp 44 and handle 46 in their assembled configuration.

Figure 20A:
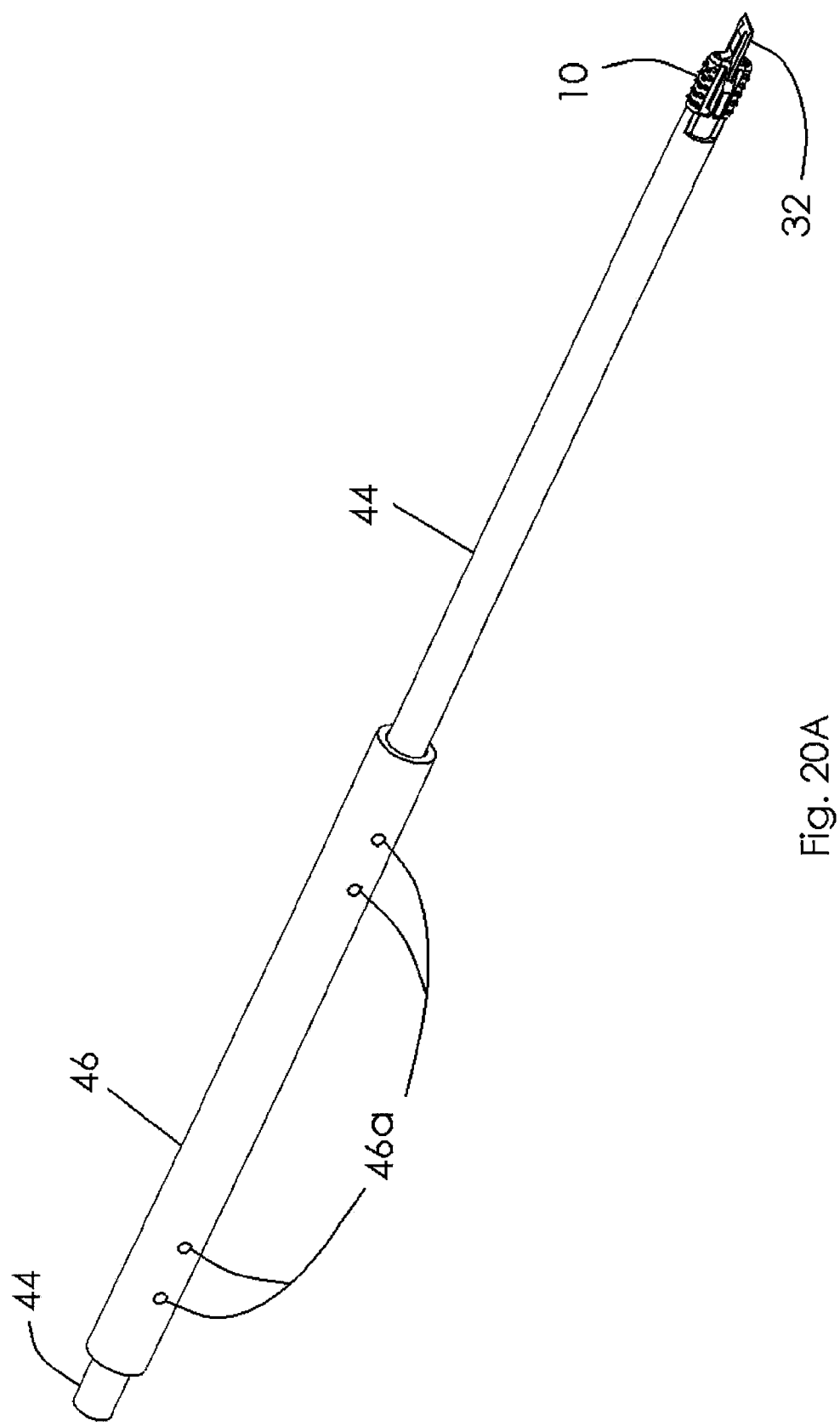
FIG. 20A is a perspective view of the one step assembly with the implant loaded onto the implant holder.

FIG. 20A is similar to FIG. 19 but it depicts implant 10 engaged to the distal end of implant holder 26.

Figure 20B:
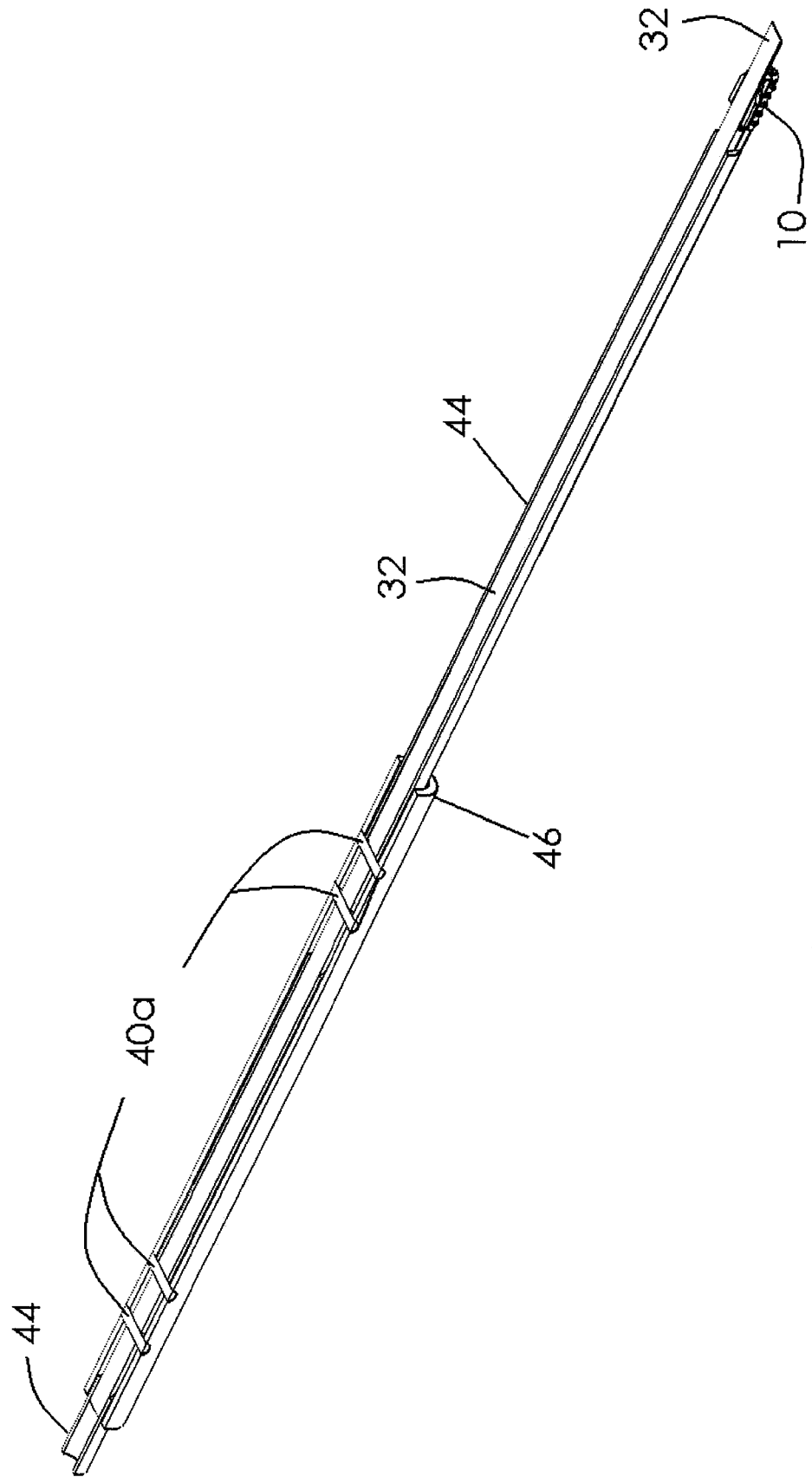
FIG. 20B is a longitudinal sectional view of the structure depicted in FIG. 20A.

FIG. 20B is a longitudinal sectional view of the structure depicted in FIG. 20A.

Figure 20C:
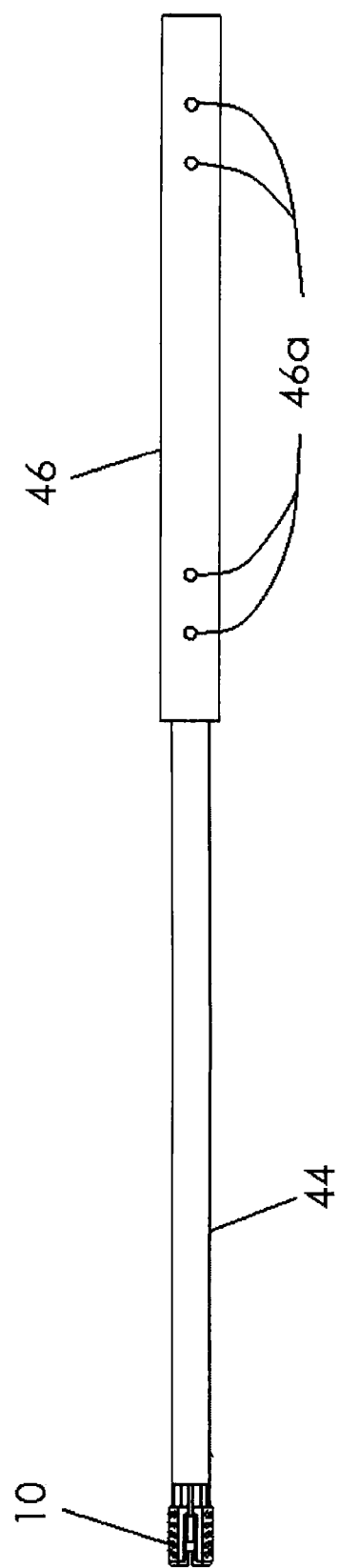
FIG. 20C is a top plan view of the structure depicted in FIG. 20A.

FIG. 20C depicts implant tamp 44 flush with handle 46. Implant 10 is depicted ejected over facet distractor 32.

Figure 20D:
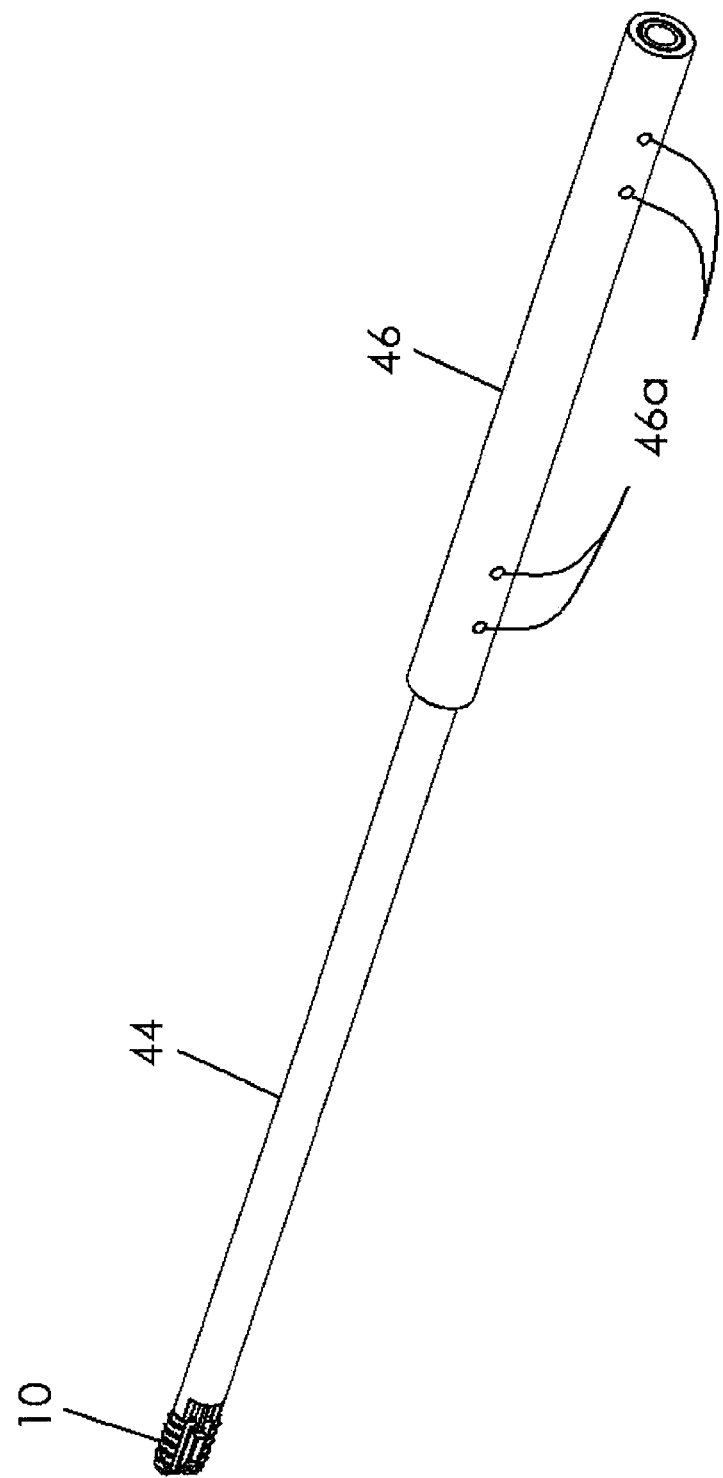
FIG. 20D is a perspective view of the one step assembly with the sleeve and implant in the final or ejected position.
Figure 20E:
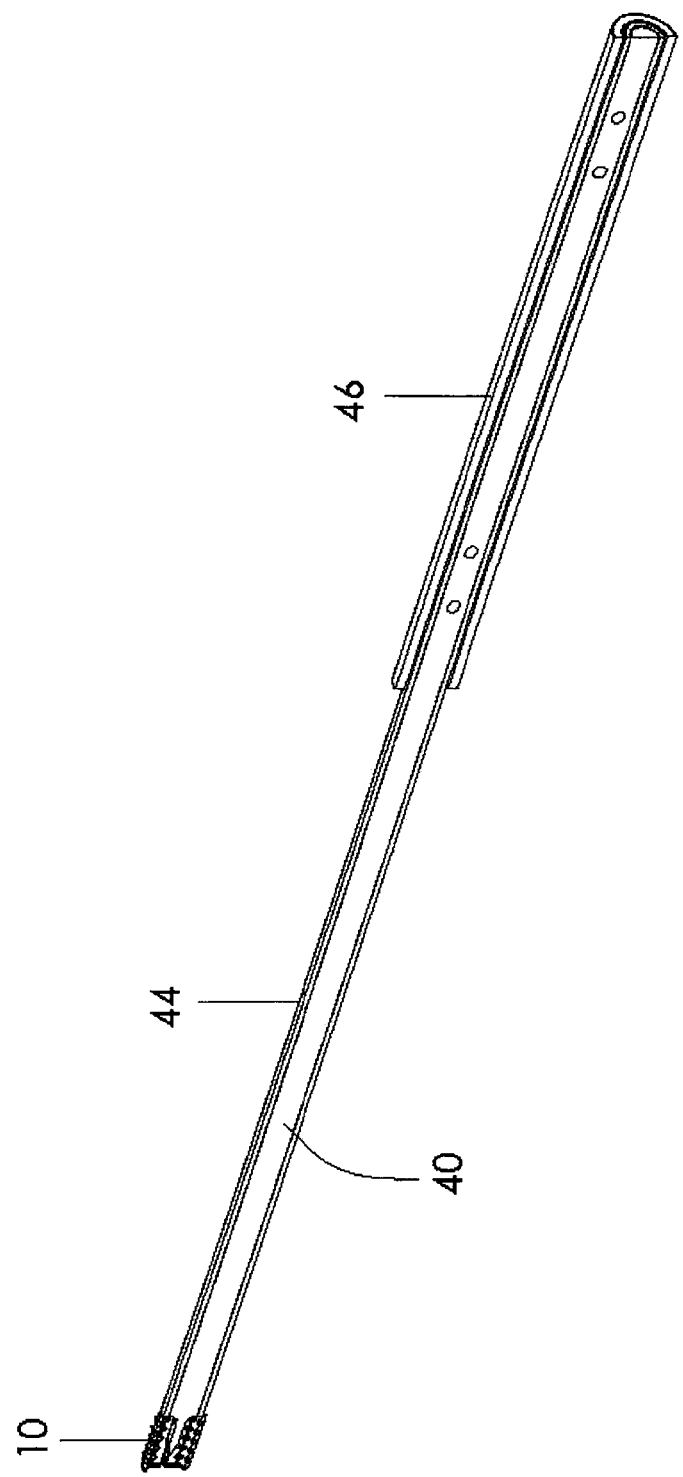
FIG. 20E is a longitudinal sectional view of the structure depicted in FIG. 20D.
Figure 21A:
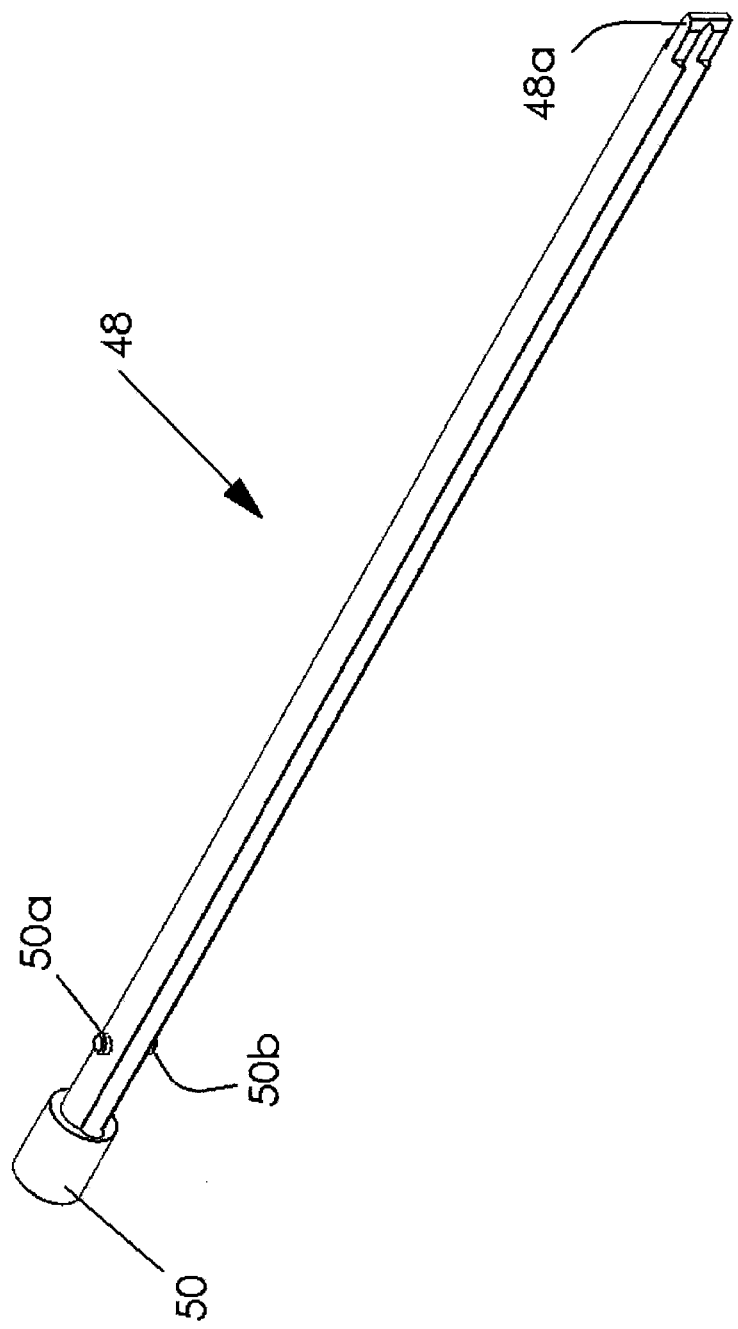
FIG. 21A is a perspective view of the drill guide with blade on tip to stabilize the drill bit in the joint.
Figure 21B:
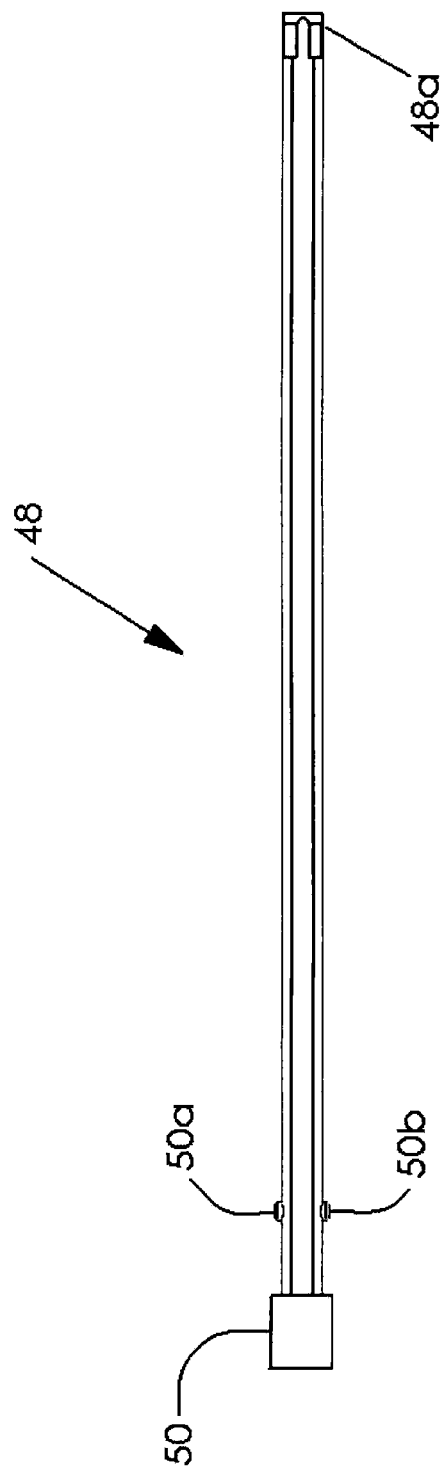
FIG. 21B is a top plan view thereof.
Figure 21C:
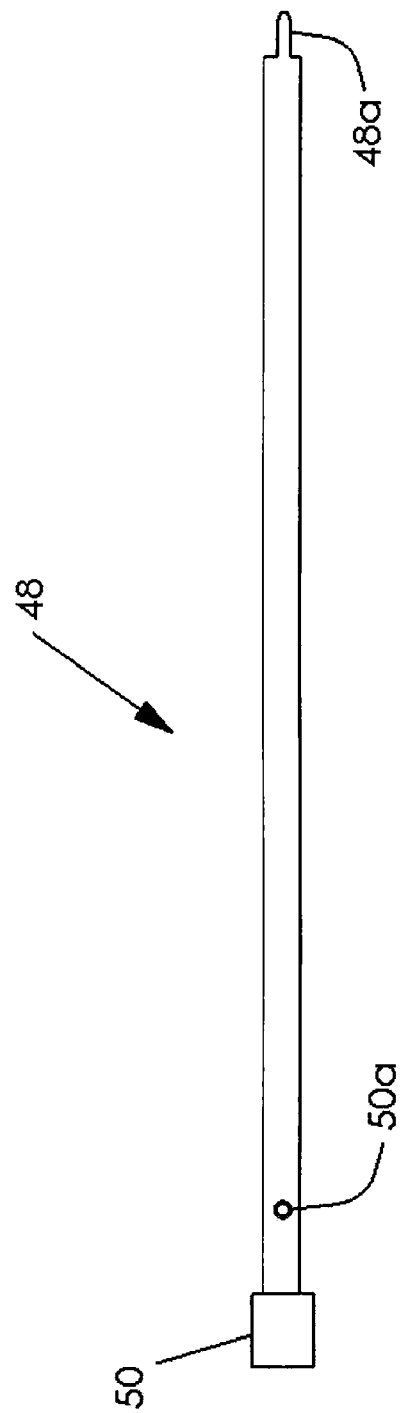
FIG. 21C is a side elevational view thereof.

FIG. 20D is a longitudinal sectional view of the structure depicted in FIG. 20E;

FIGS. 21A-C depict an alternative embodiment of drill guide 36 depicted in FIGS. 14A-D. This embodiment is denoted 48 and has blade 48a. Two opposed alignment pins 50a, 50b are formed in drill guide 48 near handle 50. The alignment pins allow insertion into directional cannula 30 at zero degrees (0°) or one hundred eighty degrees) (180°).

Figure 22A:
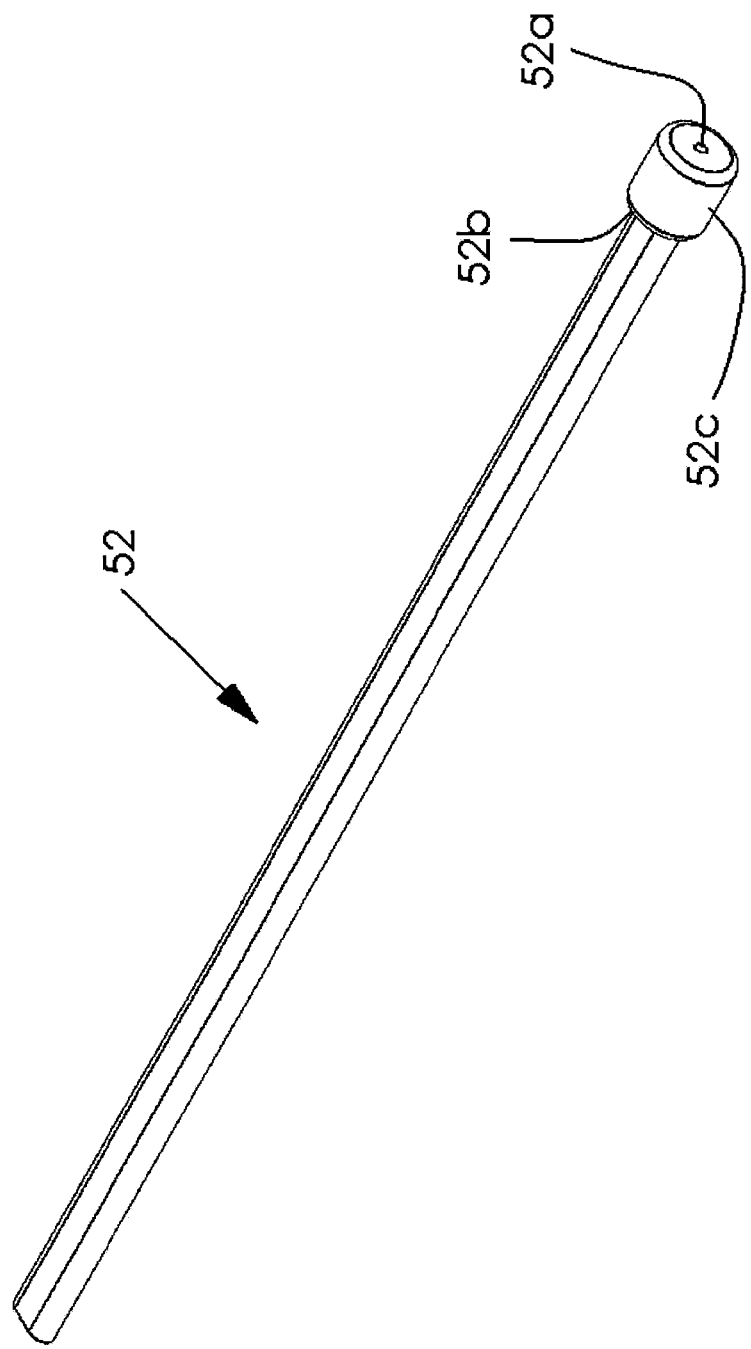
FIG. 22A is a second embodiment of the implant tamp or implant positioner where the shaft is shaped like the main body of the implant and the shaft is cannulated to allow injection of bone growth stimulation product.

FIG. 22A depicts a second embodiment, denoted 52, of implant tamp 44. The shaft of implant tamp 52 shaft conforms to main body 12 and said shaft is cannulated as at 52a to enable injection of growth stimulation product. The handle of implant tamp 52 is denoted 54.

Figure 22B:
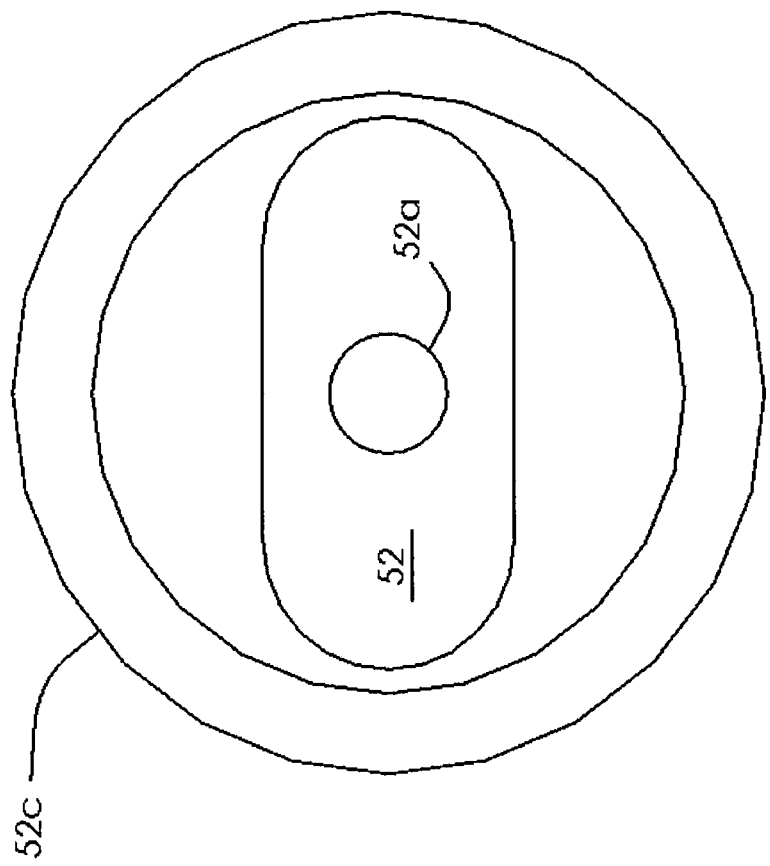
FIG. 22B is an end view of the structure depicted in FIG. 22A.

FIG. 22B provides an end view of the structure depicted in FIG. 22A.

Figure 23A:
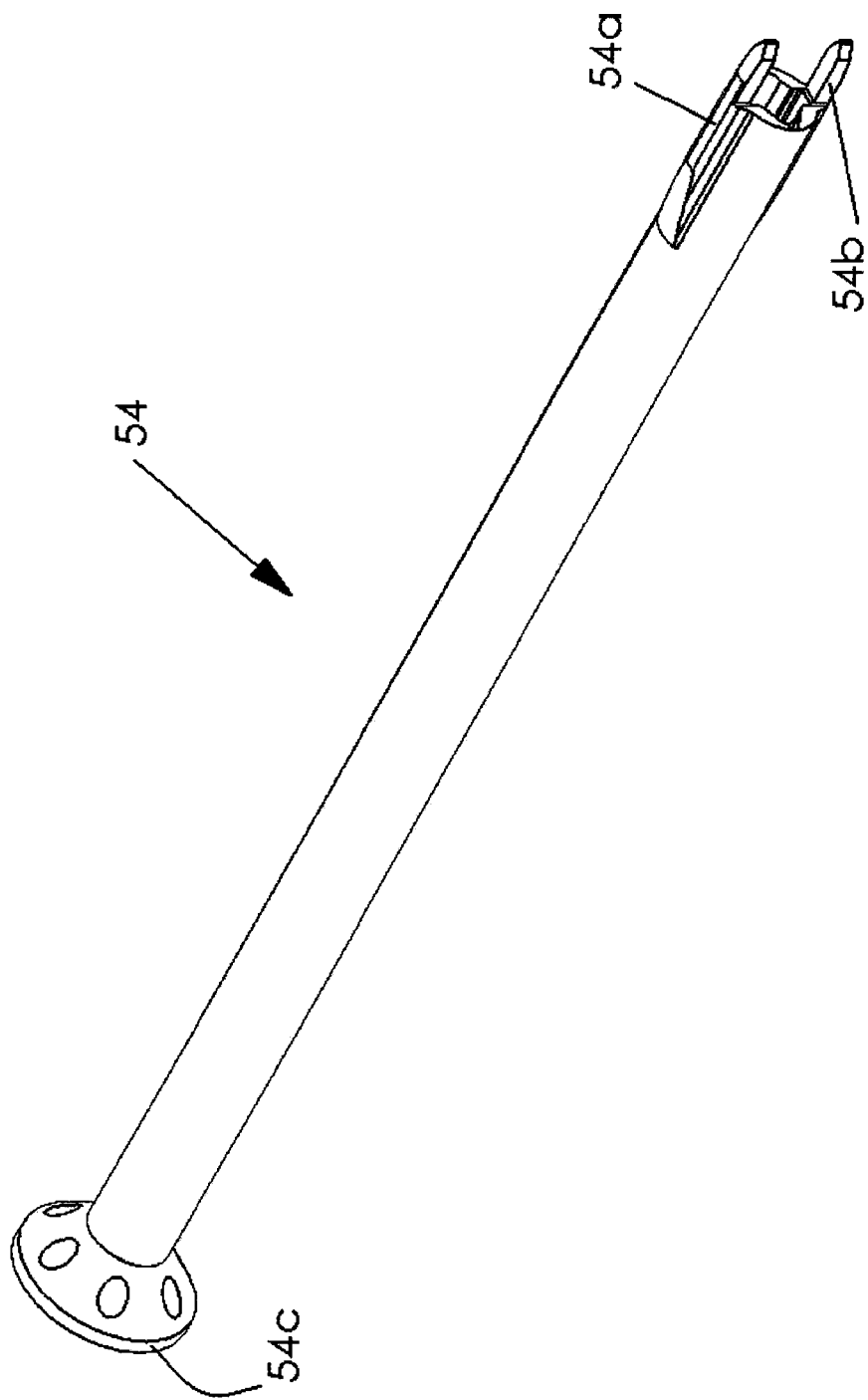
FIG. 23A is a perspective view of a second embodiment of the directional cannula.

A second embodiment of directional cannula 30 is depicted in FIG. 23 and is denoted 54. Transversely opposed distraction blades 54a, 54b are formed in its distal end and handle 56 is mounted thereto at its proximal end. The transverse cross-sectional shape of directional cannula 30 matches the transverse cross-sectional shape of implant 10.

Figure 24:
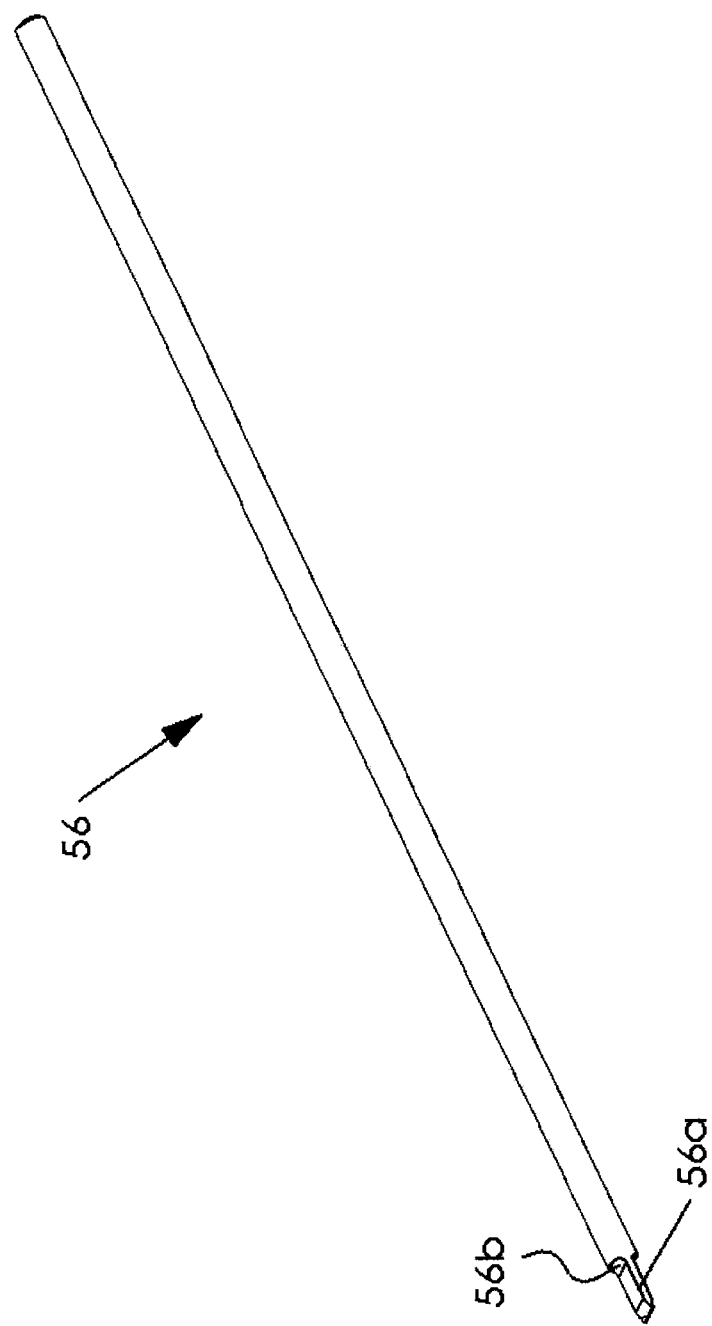
FIG. 24 is a perspective view of a second embodiment of the facet distractor.

A second embodiment of facet distractor 32 is depicted in FIG. 24 and is denoted 56. It includes blade 56a and positive stop 56b.

Figure 25:
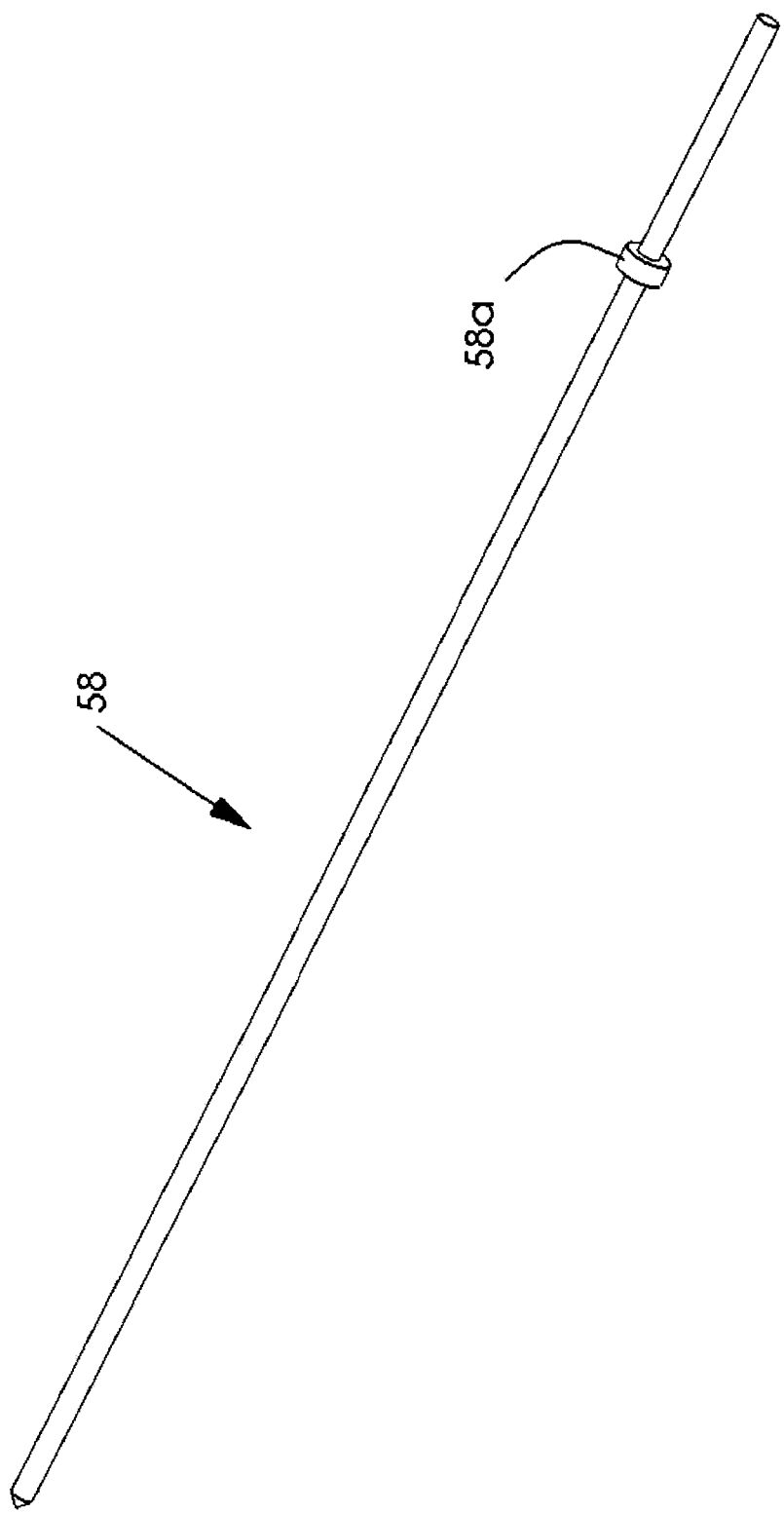
FIG. 25 is a perspective view of a drill bit.

Drill bit 58 having positive stop 58a is depicted in FIG. 25.

At least one of the instruments includes a directional feature that is used to maintain the alignment of the instrumentation with vertical plane 18 of the facet joint. By way of example but not limitation, directional cannula 30 may include a flat portion and the remaining instruments may include a flat portion on an opposite portion of the instrument so that the instruments may only be inserted through said directional cannula at zero degrees (0°) or one hundred eighty degrees)(180°).

After the proper position for cavity 20 has been identified, a drill (or reamer, punch, dremel, router, burr, etc.) is used to form cavity 20 in the facet joint. Cavity 20 is formed across vertical plane 18 so that substantially one-half of cavity 20 is formed in a first facet 22a, and substantially one-half is formed in opposing facet 22b.

Figure 8B:
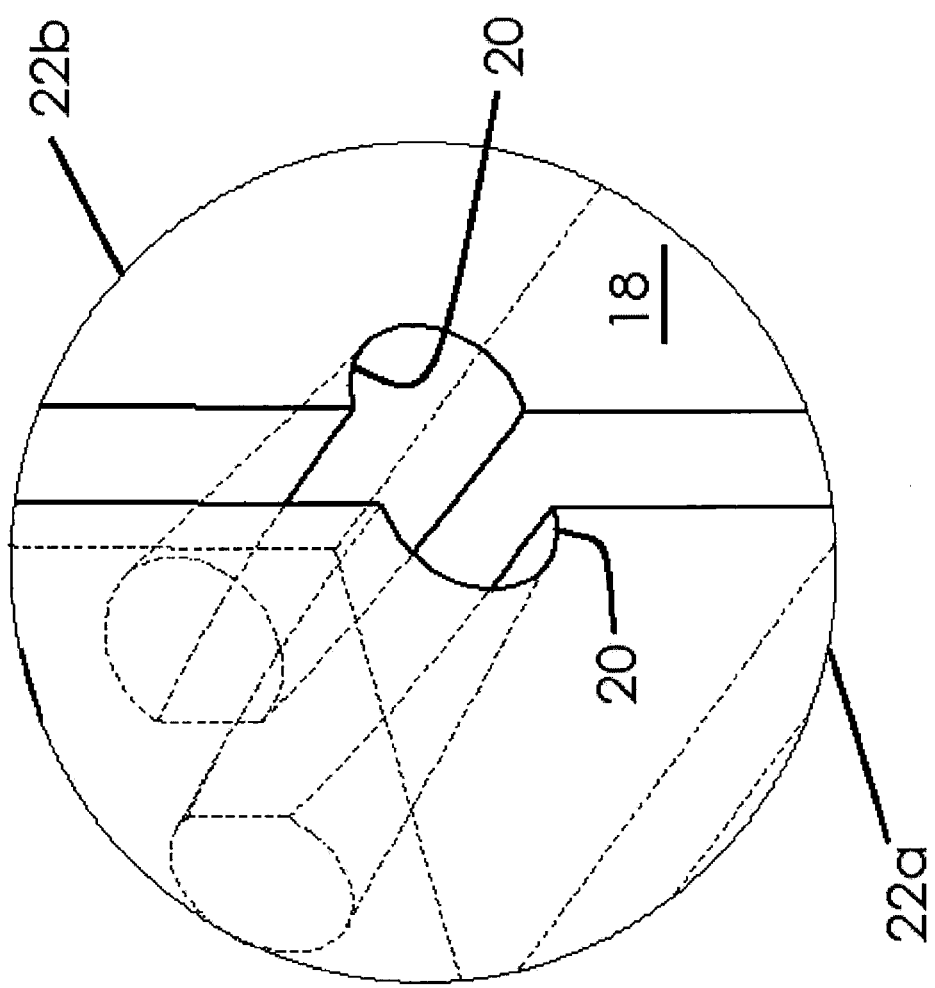
FIG. 8B is a diagrammatic perspective view of said facet joints and said cavity.
Figure 8C:
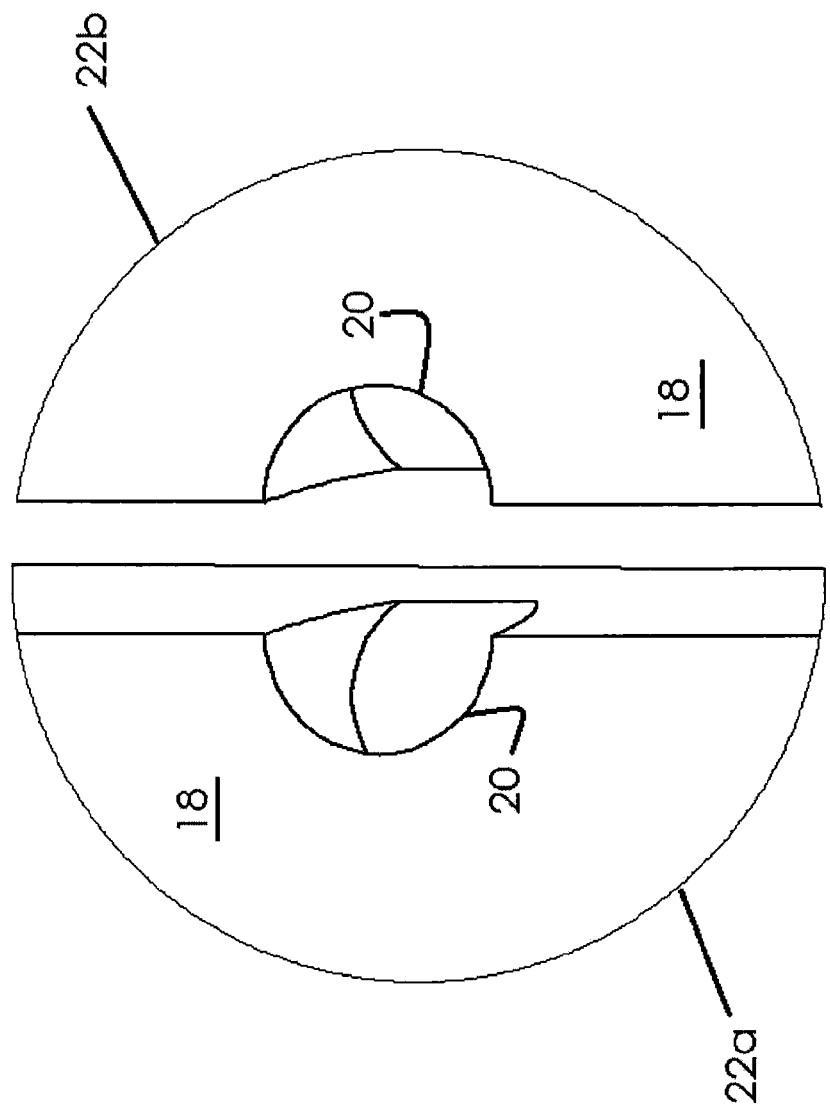
FIG. 8C is a diagrammatic front view of said facet joints and said cavity.
Figure 8D:
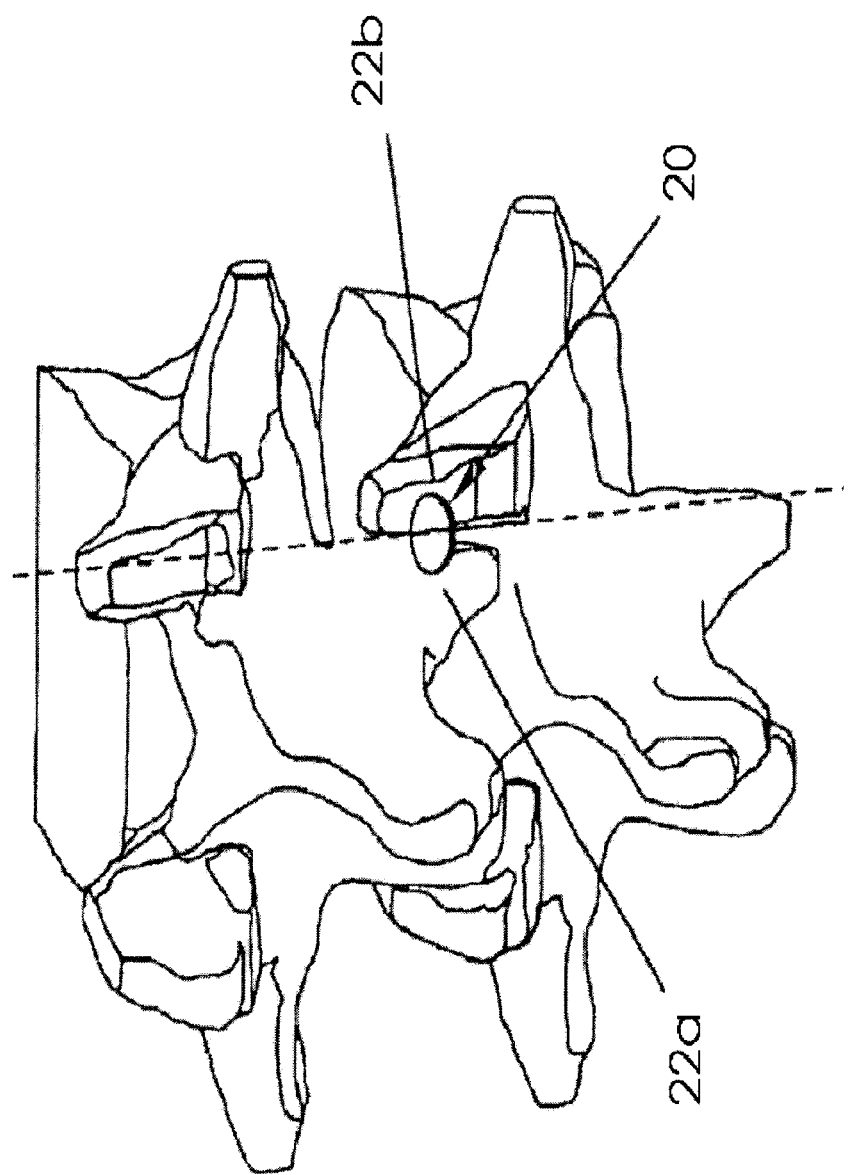
FIG. 8D is a perspective view of a superior and inferior facet joint.

After cavity 20 has been formed in (or, perhaps more literally, across) the facet joint, fusion implant 10 is inserted into cavity 20 as perhaps best understood in connection with FIG. 8D. More particularly, fusion implant 10 is inserted into cavity 20 so that main body 12 spans the gap between opposing facets 22a, 22b, and so that stabilizers 14a, 14b extend between the opposing facet surfaces. Preferably, fusion implant 10 is slightly oversized relative to cavity 20 to create a press fit.

Fusion implant 10 provides the stability and strength needed to immobilize the facet joint while fusion occurs. Due to the positioning of stabilizers 14a, 14b between the opposing facet surfaces, and due to the non-circular cross-section of main body 12, fusion implant 10 will be held against rotation within cavity 20, which will in turn hold facets 22a, 22b stable relative to one another.

When a hollow fusion implant is used, and where the implant is formed of a sufficiently strong and rigid material, cavity 20 need not be pre-formed in the opposing facets. The hollow fusion implant can be simply tapped into place, in much the same manner that a punch is used.

The novel structure provides a new and improved fusion implant for facilitating facet fusion. This novel fusion implant withstands greater forces, prohibits motion in all directions and substantially reduces the risk of implant failure. The new fusion implant also eliminates the possibility of slippage during spinal motion, greatly improves facet stability and promotes better facet fusion.

It should be appreciated that the new fusion implant combines two unique "shapes" in one implant (i.e., the shape of main body 12 and the shape of stabilizers 14a, 14b) in order to limit motion in a multidirectional joint. More particularly, the shape of main body 12 limits motion (e.g., in flexion/extension for the lumbar facets and in axial rotation for the cervical facets), while the shape of stabilizers 14a, 14b (i.e., the "keel") rests between two bony structures (i.e., in the gap of the facet joint) and limits lateral bending. This novel construction eliminates the possibility of eccentric forces inducing motion in the facet joint.

Moreover, although the novel structure effectively stabilizes the joint, it still allows the "micro motion" which is required for the fusion process to begin.

It should be appreciated that the novel fusion implant may be manufactured in a wide range of different sizes in order to accommodate any size of facet joint. Furthermore, the scale and aspect ratio of main body 12, stabilizers 14a, 14b, may be varied without departing from the scope of the present invention. Additionally, the novel fusion implant may be constructed out of any substantially biocompatible material which has properties consistent with the present invention including, but not limited to, allograft, autograft, synthetic bone, simulated bone material, biocomposites, ceramics, PEEK, stainless steel and titanium. Thus, the novel structure permits a surgeon to select a fusion implant having the appropriate size and composition for a given facet fusion.

Detailed Surgical Technique (Solid Fusion Implant)

A preferred surgical technique for using a solid fusion implant 10 will now be disclosed. The preferred surgical technique preferably uses guide pin 34 (FIG. 13) facet distractor 32 (FIG. 12), directional cannula 30 (FIG. 11), drill guide 36 (FIGS. 14A-D), implant loading block 24 (FIG. 9), implant holder 26 (FIG. 10) implant tamp 44 (FIG. 17), and tapping cap 38 (FIGS. 15A-C).

First, the facet joint is localized indirectly by fluoroscopy, or directly by visualization during an open procedure. Next, guide pin 34 (FIG. 13) is inserted into the gap between the opposing facet surfaces. The position of guide pin 34 is verified by viewing the coronal and sagittal planes. Then guide pin 34 is lightly tapped to insert the guide pin approximately five millimeters (5 mm) into the facet joint, along vertical plane 18. The inferior facet is curved medially and helps prevent guide pin 34 from damaging nerve structures.

Cannulated facet distractor 32 is then slid over guide pin 34 so that it is aligned with the vertical plane of the facet joint. Then facet distractor 32 is lightly tapped into the facet joint, along vertical plane 18.

Next, directional cannula 30 is placed over facet distractor 32 (FIG. ?) and the tip of directional cannula 30 is pushed into the facet joint (FIG. ?). Once the tip of directional cannula 30 has entered the facet joint, the directional cannula is lightly tapped so as to seat the cannula in the facet joint. This aligns directional cannula 30 with the vertical plane of the facet joint. After verifying that directional cannula 30 has been inserted all the way into the facet joint and is stabilized in the joint, facet distractor 32 is removed.

Drill guide 36 is then inserted into directional cannula 30. Drill guide 36 is advanced within directional cannula 30 until a drill guide stop is resting on directional cannula 30. Then, with drill guide 36 in place, irrigation (e.g., a few drops of saline) is placed into drill guide. Next, drill bit 58 is used to drill a cavity 20. This is done by drilling until drill bit 58 reaches the mechanical stop on drill guide 36 (FIGS. 21A-B). Drill guide 36 and drill bit 58 are then pulled out of directional cannula 30, drill guide 36 is rotated 180 degrees, and drill guide 36 is reinserted into directional cannula 30 in order to drill the superior facet. With drill guide 36 in place, irrigation (e.g., a few drops of saline) is placed into said drill guide, and drill bit 58 is used to drill cavity 20 in the superior facet. Again, drilling occurs until drill bit 58 reaches the mechanical stop on drill guide 36. Drill bit 58 is then removed.

Figure 26:
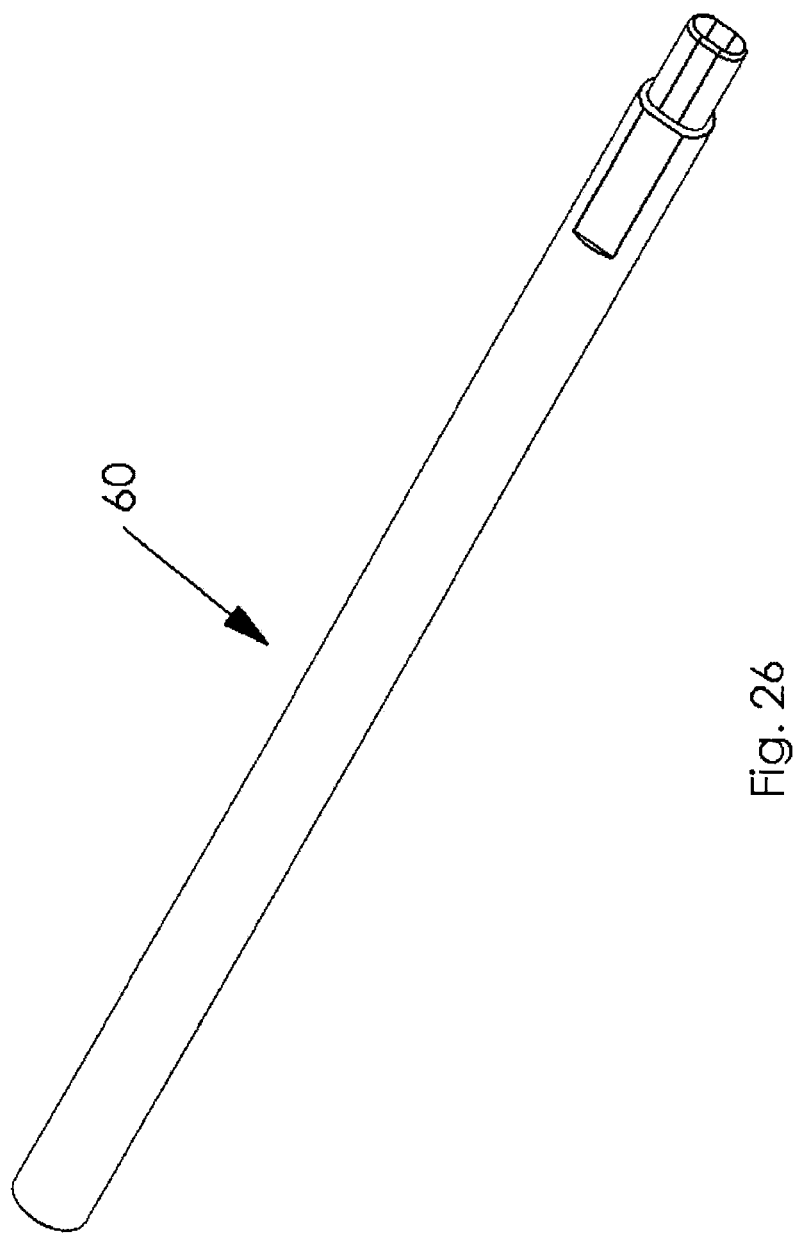
FIG. 26 is a perspective view of a cavity cutter.

Cavity cutter 60, depicted in FIG. 26, may replace drill guide 36 and drill bit 58 to make an opening having the perfect shape for fusion implant 10.

Using implant loading block 24 depicted in FIG. 9, fusion implant 10 is then inserted into implant holder 26. Implant holder 26, with fusion implant 10 in place, is then placed into directional cannula 30. Next, implant holder 26 is lightly tapped so as to insert fusion implant 10 into cavity 20 created in the facet joint. Once the implant has been positioned in cavity 20, implant tamp 44 is inserted into implant holder 26. Next, implant tamp 44 is lightly tapped so as to drive the implant into cavity 20. The implant is preferably countersunk 1-2 mm into the facet joint.

Implant tamp 44, implant holder 26 and directional cannula 30 are removed from the surgical site and the incision is closed to conclude the procedure.

Detailed Surgical Technique (Hollow Fusion Implant)

A preferred surgical technique for using a hollow fusion implant 10 will now be disclosed. The preferred surgical technique preferably uses guide pin 34 (optional) (FIG. 13), one step facet distractor and implant holder 40 (FIG. 16A), implant tamp 44 (FIG. 17), and handle 46 (FIG. 17).

First, the facet joint is localized indirectly by fluoroscopy or directly by visualization during an open procedure. The following step involving use of guide pin 34 is entirely optional. If used, guide pin 34 is inserted in the gap between the opposing facet surfaces. The position of guide pin 34 is verified by viewing the coronal and sagittal planes. Guide pin 34 is then lightly tapped so as to insert said guide pin approximately five millimeters (5 mm) into the facet joint, along the vertical plane of the facet joint. The inferior facet curves medially and helps prevent the guide pin from damaging nerve structures.

One step facet distractor with implant holder 40, which may be cannulated or not cannulated, is then slid over guide pin 34, if used, so that it is aligned with the vertical plane of the facet joint. Facet distractor 32 is lightly tapped into the facet joint, along the vertical plane of the facet joint. This step may be accomplished without use of guide pin 34.

Next, facet distractor with implant holder 40, implant tamp 44, handle 46 assembly, with hollow fusion implant 10 mounted thereto (FIG. 20A) is pushed, hammered, or otherwise advanced downwards to drive hollow fusion implant 10 into the facet joint.

Finally, the facet distractor/implant tamp assembly is removed, leaving hollow fusion implant 10 in the facet joint, and the incision is closed.

The following procedure applies to both solid or hollow implants.

Performing posterior facet fusion with the novel tools is a nine step procedure.

In the first step, the facet joint is localized either indirectly using fluoroscopy or directly by visualization during an open procedure. Facet distractor 56 is then inserted into the plane of the facet joint. Placement is verified by viewing in the coronal and sagittal plane. The inferior facet curves medially and should prevent guide pin 34 from being advanced into nerve structures. Tapping cap 38 is then tapped lightly so that blade 56a of facet distractor 56a enters into the plane of the facet joint. If necessary, the shallow end 38c of the tapping cap can be used to seat the facet distractor. Positive stop 56b is formed in facet distractor 56 to prevent it from being advanced into the nerve structures.

In step three, directional cannula 54 is placed over facet distractor 56. Tip 56a of facet distractor 56 is aligned with tips 54a, 54b of directional cannula 54 and is lightly pushed into the facet joint. After tips 54a, 54b have entered into the facet joint, directional cannula 54 is lightly tapped to fully seat it. If necessary, the deep end 38a of tapping cap 38a can be used to seat the directional cannula.

The insertion of directional cannula 54 all the way into the facet joint is then verified. Facet distractor 56 is removed after such positioning is verified.

In step four, drill guide 36 is inserted into the lumen of directional cannula 54, aligning pins 50a, 50b into slots 54a, 54b formed in directional cannula 54. The insertion continues until drill guide positive stop 36b abuts directional cannula 54 and blade 48a is in the facet joint.

Step five is the drilling of the inferior facet. With drill guide 36 in place upon the completion of step four. Cavity 20 is then drilled by drill bit 58 into the inferior facet. Drilling continues until drill bit 58 abuts positive stop 58*a*. Drill guide 36 is held down when drill bit 58 is removed and said drill bit is not removed until it has stopped rotating.

Drill guide 36 and drill bit 58 are pulled from directional cannula 54 in step six and it is cleaned to remove tissue. It is then rotated one hundred eighty degrees (180°) and re-inserted into directional cannula 30.

Cavity 20 is drilled into the superior facet in step seven. A few drops of irrigation (saline) are placed into the drill guide. Said cavity is then drilled by drill bit 58 into the superior facet. Drilling continues until drill bit 58 abuts positive stop 58*a*. Drill guide 36 is held down when drill bit 58 is removed and said drill bit is not removed until it has stopped rotating.

In step eight, an implant is loaded into directional cannula 54 with the chamfer 16 pointed downward. Implant tamp 52 is inserted into the lumen of directional cannula 54. Implant tamp 52 is lightly tapped until it reaches positive stop 52*b* to fully seat implant 10 in cavity 20. Implant tamp 52 and directional cannula 54 are then removed.

Numerous advantages are achieved by the present invention. Among other things, the present invention provides a fast, simple, minimally-invasive and easily reproduced approach for effecting facet fusion.

While fusion implant 10 has been disclosed in the context of fusing a facet joint, it should also be appreciated that fusion implant 10 may be used to stabilize and fuse any joint having anatomy similar to the facet joint, i.e., a pair of opposing bony surfaces defining a gap therebetween, with the stabilizer of the fusion implant being sized to be positioned within the gap. By way of example but not limitation, the fusion implant may be used in small joints such as the fingers, toes, etc.

Many additional changes in the details, materials, steps and arrangements of parts, which have been herein disclosed in order to explain the nature of the present invention, may be made by those skilled in the art while still remaining within the principles and scope of the invention.

It will be seen that the advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A spinal facet fusion implant adapted to be positioned between spaced apart spinal facets that form a facet joint, comprising:
   an elongated main body having a distal end, a proximal end and a longitudinal, y-axis extending between the distal end and the proximal end, a transverse, x-axis and a z-axis perpendicular to said longitudinal and transverse axes;
   said elongated main body having longitudinally-extending, transversely opposed sides:
   at least one semi-circular cavity formed in each spinal facet of a pair of opposed, spaced apart spinal facets;
   at least one stabilizer extending radially outwardly from said elongated main body in the z-axis;
   said elongated main body having a width in the transverse axis that is less than the combined width of the spinal facets making up a facet joint;
   said elongated main body oriented so that said transversely opposed sides are disposed within said semi-circular cavities formed in said opposed, spaced apart spinal facets:
   said at least one stabilizer having a predetermined width that is sized to make a press fit into a gap between said spinal facets when said elongated main body is oriented with said transversely opposed sides disposed within said opposed semi-circular cavities.

2. A spinal facet fusion implant according to claim 1, further comprising:
   said main body being chamfered at its distal end.

3. A spinal facet fusion implant according to claim 1, further comprising:
   said main body having at least one barb formed on an external surface;
   said barb configured to permit axial insertion in the distal direction and inhibit axial retraction in the proximal direction.

4. A spinal facet fusion implant according to claim 1, further comprising:
   said main body being substantially solid.

5. A spinal facet fusion implant according to claim 4, further comprising:
   said main body having at least one bore formed therein to permit bone in-growth.

6. A spinal facet fusion implant according to claim 5, further comprising:
   said at least one bore being a cross-bore.

7. A spinal facet fusion implant according to claim 5, further comprising:
   said at least one bore being a blind bore.

8. A spinal facet fusion implant according to claim 5, further comprising:
   said at least one bore being filled with a bone growth promoter.

9. A spinal facet fusion implant according to claim 1, further comprising:
   said main body being substantially hollow.

10. A spinal facet fusion implant according to claim 9, further comprising:
    said main body having at least one bore formed therein to permit bone in-growth.

11. A spinal facet fusion implant according to claim 10, further comprising:
    said at least one bore being a cross-bore.

12. A spinal facet fusion implant according to claim 10, further comprising:
    said at least one bore being a blind bore.

13. A spinal facet fusion implant according to claim 10, further comprising:
    said at least one bore being filled with a bone growth promoter.

14. A spinal facet fusion implant according to claim 1, further comprising:
    at least one step formed in said main body.

15. A spinal facet fusion implant according to claim 14, further comprising:
    said step extending parallel to said longitudinal axis.

16. A spinal facet fusion implant according to claim 14, further comprising:
    said step extending perpendicular to said longitudinal axis.

17. A spinal facet fusion implant according to claim 14, further comprising:
    said step extending transverse to said longitudinal axis.

18. A spinal facet fusion implant according to claim 1, further comprising:
    said transverse axis exceeding said z-axis in length.

19. A spinal facet fusion implant according to claim 1, further comprising:

said stabilizer positioned in said z-axis exceeding said transverse axis in length.

20. A spinal facet fusion implant according to claim 1, further comprising:
said main body having a noncircular transverse cross-section.

21. A spinal facet fusion implant according to claim 1, further comprising:
said main body having a rectangular transverse cross-section.

22. A spinal facet fusion implant according to claim 1, further comprising:
said main body having a rounded rectangular transverse cross-section.

23. A spinal facet fusion implant according to claim 1, further comprising:
said main body having an ovoid form in transverse cross-section.

24. A spinal facet fusion implant according to claim 1, further comprising:
said main body having a triangular transverse cross-section.

25. A spinal facet fusion implant according to claim 1, further comprising:
said main body having a circular form in transverse cross-section.

26. A spinal facet fusion implant according to claim 1, further comprising:
said at least one stabilizer extending upwardly from said main body.

27. A spinal facet fusion implant according to claim 1, further comprising:
said at least one stabilizer depending from said main body.

28. A spinal facet fusion implant according to claim 1, further comprising:
said fusion device including a pair of stabilizers.

29. A spinal facet fusion implant according to claim 28, further comprising:
said pair of stabilizers being diametrically opposed to one another.

30. A spinal facet fusion implant according to claim 1, further comprising:
said spinal facet fusion implant including a fixation device for securing the spinal facet fusion implant in the facet joint.

31. A spinal facet fusion implant according to claim 30, further comprising:
said fixation device being a screw.

32. A method for fusing a spinal facet joint defined by a pair of spinal facets, comprising the steps of:
providing a spinal facet fusion implant having an elongated main body, said main body having a distal end, a proximal end and a longitudinal axis extending between the distal end and the proximal end, the elongated body having a cross-sectional profile characterized by a primary axis and a secondary axis;
providing at least one stabilizer extending radially outwardly from said main body in the secondary axis;
forming said main body so that it has a length along the primary axis which is less than the combined width of said pair of spinal facets;
forming said at least one stabilizer so that it has a width which is sized to make a press fit into the gap between said pair of spinal facets;
deploying the spinal facet fusion implant in said facet joint so that said main body is simultaneously positioned within both of the facets of the facet joint and said at least one stabilizer is positioned within a natural gap between said spinal facets; and
maintaining the spinal facet fusion implant in said gap while fusion occurs.

33. The method according to claim 32, further comprising the step of:
forming a bore in said pair of spinal facets;
installing the spinal facet fusion implant in said bore.

34. The method according to claim 32, further comprising the step of:
installing the spinal facet fusion implant into virgin bone of the spinal facets.

35. A spinal facet fusion implant for positioning between spinal facets that form a facet joint, comprising:
an elongated main body having a distal end, a proximal end and a longitudinal axis extending between the distal end and the proximal end, said main body having a cross-sectional profile having a primary axis and a secondary axis;
said main body having a length along the primary axis that is less than the combined width of said spinal facets;
said main body being non-circular in transverse section and having transversely opposed sides;
a semi-circular cavity formed in each facet of opposed, spaced apart joint facets;
said main body oriented so that said transversely opposed sides are respectively disposed within said semi-circular cavities;
said spinal facet fusion implant deployed in a facet joint so that said main body is positioned between said pair of spinal facets; and
said spinal facet fusion implant maintained between said pair of spinal facets while fusion occurs.

36. A method for fusing a spinal facet joint formed by a pair of spinal facets, comprising the steps of:
providing a spinal facet fusion implant;
forming said spinal facet fusion implant so that it includes a main body having a distal end, a proximal end and a longitudinal axis extending between the distal end and the proximal end, said main body having a cross-sectional profile characterized by a primary axis and a secondary axis;
forming said main body so that it has a length along the primary axis that is less than the combined width of said pair of spinal facets;
forming said main body so that it is non-circular in transverse cross-section;
providing said main body with transversely opposed sides;
forming a semi-circular cavity in each facet of opposed, spaced apart joint facets;
orienting said main body so that said transversely opposed sides are respectively disposed within said semi-circular cavities;
deploying the spinal facet fusion implant in a facet joint so that said main body is positioned between said pair of spinal facets; and
maintaining the spinal facet fusion implant between said pair of spinal facets while fusion occurs.

37. A joint fusion implant for positioning between opposing joint facets, comprising:
an elongated main body having a distal end, a proximal end and a longitudinal axis extending between the distal end and the proximal end, the main body having a cross-sectional profile characterized by a primary axis and a secondary axis;

said elongated main body having longitudinally-extending, transversely opposed sides:
at least one stabilizer extending radially outwardly from the main body in the secondary axis;
said elongated main body having a length along the primary axis that is less than a combined width of bones making up a joint;
said elongated main body oriented so that said transversely opposed sides are disposed within opposed semi-circular cavities formed in said spaced apart joint facets;
said at least one stabilizer having a width that is sized to make a press fit into a gap between the bones making up the joint facets when said elongated main body is oriented with said transversely opposed sides disposed within said opposed semi-circular cavities.

38. A method for fusing a joint, comprising the steps of:
providing a fusion implant having an elongated main body;
forming said elongated main body so that it has a distal end, a proximal end and a longitudinal axis extending between the distal end and the proximal end, the elongated main body having a cross-sectional profile characterized by a primary axis and a secondary axis;
providing at least one stabilizer extending radially outwardly from the elongated main body in the secondary axis;
forming said main body so that it has a length along the primary axis that is less than the combined width of the bones making up said joint;
forming said at least one stabilizer so that it has a width that is sized to make a press fit into a gap between bones that form said joint;
forming a semi-circular cavity in opposing bones that collectively form said joint;
deploying the fusion implant in said joint so that said opposite sides of said main body are simultaneously positioned within said semi-circular cavities and the at least one stabilizer is positioned within a gap between the bones; and
maintaining the fusion implant in said joint while fusion occurs.

\* \* \* \* \*